United States Patent [19]
Sasaki et al.

[11] Patent Number: 5,654,136
[45] Date of Patent: Aug. 5, 1997

[54] ATTENUATED MEASLES VIRUS VACCINE, CONTAINING SPECIFIC NUCLEOTIDE SEQUENCE AND A METHOD FOR ITS ABSOLUTE IDENTIFICATION

[75] Inventors: Keiko Sasaki; Takayuki Mori; Satoshi Makino, all of Tokyo, Japan

[73] Assignee: The Kitasato Institute, Tokyo, Japan

[21] Appl. No.: 348,891

[22] Filed: Nov. 25, 1994

Related U.S. Application Data

[63] Continuation of Ser. No. 848,400, Mar. 10, 1992, abandoned

[30] Foreign Application Priority Data

Oct. 14, 1991 [JP] Japan ................................. 3-293625

[51] Int. Cl.$^6$ ........................... C12Q 1/70; C12N 15/45
[52] U.S. Cl. ........................................ 435/5; 536/23.72
[58] Field of Search ............................... 435/5, 6, 237, 435/320.1; 536/23.72

[56] References Cited

U.S. PATENT DOCUMENTS 4,617,261  10/1986  Sheldon et al. ................. 435/6
4,985,244   1/1991  Makino et al. ................ 424/202.1

FOREIGN PATENT DOCUMENTS 0440219  8/1991  European Pat. Off. .

OTHER PUBLICATIONS

By S. Makino et al., "Studies of the Live Aik Measles Vaccine", 1974, vol. 47, Nos. 1–2, pp. 13–21, The Kitasato Insitutue, Tokyo, Japan.
A. Schmid et al., "A procedure for selective full length cDNA cloning of specific RNA species", 1987, vol. 15, No. 10, pp. 3987–3996, IRL Press Limited, Oxford, England.
By D. Mack et al., "Novel Viruses", 1990, pp. 378–385, PCR Protocols: A Guide to Methods and Applications, Academic Press, Inc.
By S. Makino et al., "Cultivation of Measles Virus in Sheep Kidney Cells", 1970, vol. 14, No. 6, pp. 501–504, Japanese Journal of Microbiology.

By S. Makino et al., "Field Trial with a Fruther Attenuated Live Measles Virus Vaccine", 1973, vol. 27, No. 1, pp. 75–79, Japanese Journal of Microbiology.
Cattaneo et al. Virology, 173(2):415–25, Dec. 1989, Abstract and Sequence Search Results pp. 1–31.
"Propagation in Tissue Cultures of Cytopathogenic Agents from Patients with Measles", *Cytopathogenic Agents from Measles Cases*, By J. Enders et al., pp. 277–286.
"Studies on an Attenuated Measles–Virus Vaccine", *New England Journal of Medicine*, vol. 263, 1960, By J. Enders et al., pp. 153–184.
"Cultivation of Measles Virus in Sheep Kidney Cells", *Japan J. Microbiol.*, vol. 14, No. 6, 1970, By S. Makino et al., pp. 501–504.
"Field Trial with a Further Attenuated Live Measles Virus Vaccine" *Japan J. Microbiol.*, vol. 17, No. 1, 1973, By S. Makino et al., pp. 75–79.
"Studies on the Modification of the Live AIK Measles Vaccine", *Kitasato Arch. of Exp. Med.*, vol. 47, Nos. 1–2, 1974, By K. Sasaki, pp. 1–12.
"Studies on the Modification of the Live AIK Measles Vaccine", *Kitasato Arch. of Exp. Med.*, vol. 47, Nos. 1–2, 1974, By S. Makino et al., pp. 13–21.
"Measles Vaccine Used in Japan", *Reviews of Infectious Diseases*, vol. 5, No. 3, May–Jun. 1983, By M. Hirayama, pp. 495–503.
"Development and Characteristics of Live AIK–C Measles Virus Vaccine A Brief Report", *Reviews of Infectious Diseases*, vol. 5, No. 3, May–Jun. 1983, By S. Makino, pp. 504–505.

*Primary Examiner*—Mindy Fleisher
*Assistant Examiner*—Terry A. McKelvey
*Attorney, Agent, or Firm*—Young & Thompson

[57] ABSTRACT

A measles vaccine virus AIK-C strain comprises genomic RNA that produces by reverse transcription cDNA having a specific nucleotide sequence indicative of the viral genomic RNA in the seed virus for measles vaccine or measles virus vaccine. The complete sequence of 15,894 nucleotides has been determined.

3 Claims, 3 Drawing Sheets

FIG. 3

| PRIMER | BASE SEQUENCE | OBTAINED cDNA |
|---|---|---|
| MP-1: | 5'—TTAGGGATATCCGAGATGGCCACAC—3' | pMN2 |
| MP-2: | 5'—CTCGGAAGAACAAGGCTCAGACAC—3' | pMP1 |
| MP-3: | 5'—GGAAGGACACCCTCTCAAGCATCATG—3' | pMM1 |
| MP-4: | 5'—GCAGCCATCAGTTCCTCAAG—3' | pMF1 |
| MP-5: | 5'—GTCTACATCCTGATTGCAGTG—3' | pMH1 |
| MP-6: | 5'—GTCAACGAGGAAGATCCGTGAACTCCTCA—3' | pML1 |
| MP-7: | 5'—GCACGATTTGACTAAGGCACTCCA—3' | pML2 |
| MP-8: | 5'—TGTCCTCATTGACAAAGAGTCATG—3' | pML3 |
| MP-9: | 5'—AGGTGCTTGTCAATGCTCTAAGCCA—3' | pML4 |
| MP-10: | 5'—CTTATCGATGGCTCTGCTCCTGGGC—3' | pML5 |
| MP-11: | 5'—TGGAAGCTTATCCAGAATCTCAAGTCCGGCT—3' | pML6 |
| BEP(dT)7: | 5'—CTGTGAATTCTGCAGGATCCCTTTTTT—3' | pMN1 |

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 15894 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 108..1682

( i x ) FEATURE:
        ( A ) NAME/KEY: CDS
        ( B ) LOCATION: 1807..3327

( i x ) FEATURE:
        ( A ) NAME/KEY: CDS
        ( B ) LOCATION: 3438..4442

( i x ) FEATURE:
        ( A ) NAME/KEY: CDS
        ( B ) LOCATION: 5458..7107

( i x ) FEATURE:
        ( A ) NAME/KEY: CDS
        ( B ) LOCATION: 7271..9121

( i x ) FEATURE:
        ( A ) NAME/KEY: CDS
        ( B ) LOCATION: 9234..15782

( x i ) SEQUENCE DESCRIPTION: SEQ ID NO:1:

```
ACCAAACAAA GTTGGGTAAG GATAGTTCAA TCAATGATCA TCTTCTAGTG CACTTAGGAT        60

TCAAGATCCT ATTATCAGGG ACAAGAGCAG GATTAGGGAT ATCCGAG ATG GCC ACA        116
                                                    Met Ala Thr
                                                     1

CTT TTA AGG AGC TTA GCA TTG TTC AAA AGA AAC AAG GAC AAA CCA CCC        164
Leu Leu Arg Ser Leu Ala Leu Phe Lys Arg Asn Lys Asp Lys Pro Pro
     5                  10                  15

ATT ACA TCA GGA TCC GGT GGA GCC ATC AGA GGA ATC AAA CAC ATT ATT        212
Ile Thr Ser Gly Ser Gly Gly Ala Ile Arg Gly Ile Lys His Ile Ile
 20              25                  30                  35

ATA GTA CCA ATC CCT GGA GAT TCC TCA ATT ACC ACT CGA TCC AGA CTT        260
Ile Val Pro Ile Pro Gly Asp Ser Ser Ile Thr Thr Arg Ser Arg Leu
                 40                  45                  50

CTG GAC CGG TTG GTC AGG TTA ATT GGA AAC CCG GAT GTG AGC GGG CCC        308
Leu Asp Arg Leu Val Arg Leu Ile Gly Asn Pro Asp Val Ser Gly Pro
             55                  60                  65
```

| | | | | | | | | | | | | | | | | |
|---|---|---|---|---|---|---|---|---|---|---|---|---|---|---|---|---|
| AAA | CTA | ACA | GGG | GCA | CTA | ATA | GGT | ATA | TTA | TCC | TTA | TTT | GTG | GAG | TCT | 356 |
| Lys | Leu | Thr<br>70 | Gly | Ala | Leu | Ile<br>75 | Gly | Ile | Leu | Ser | Leu<br>80 | Phe | Val | Glu | Ser | |
| CCA | GGT | CAA | TTG | ATT | CAG | AGG | ATC | ACC | GAT | GAC | CCT | GAC | GTT | AGC | ATA | 404 |
| Pro | Gly<br>85 | Gln | Leu | Ile | Gln | Arg<br>90 | Ile | Thr | Asp | Asp | Pro<br>95 | Asp | Val | Ser | Ile | |
| AGG | CTG | TTA | GAG | GTT | GTC | CAG | AGT | GAC | CAG | TCA | CAA | TCT | GGC | CTT | ACC | 452 |
| Arg<br>100 | Leu | Leu | Glu | Val<br>105 | Val | Gln | Ser | Asp | Gln<br>110 | Ser | Gln | Ser | Gly | Leu<br>115 | Thr | |
| TTC | GCA | TCA | AGA | GGT | ACC | AAC | ATG | GAG | GAT | GAG | GCG | GAC | AAA | TAC | TTT | 500 |
| Phe | Ala | Ser | Arg | Gly<br>120 | Thr | Asn | Met | Glu | Asp<br>125 | Glu | Ala | Asp | Lys | Tyr<br>130 | Phe | |
| TCA | CAT | GAT | GAT | CCA | ATT | AGT | AGT | GAT | CAA | TCC | AGG | TTC | GGA | TGG | TTC | 548 |
| Ser | His | Asp | Asp<br>135 | Pro | Ile | Ser | Ser | Asp<br>140 | Gln | Ser | Arg | Phe | Gly<br>145 | Trp | Phe | |
| GAG | AAC | AAG | GAA | ATC | TCA | GAT | ATT | GAA | GTG | CAA | GAC | CCT | GAG | GGA | TTC | 596 |
| Glu | Asn | Lys<br>150 | Glu | Ile | Ser | Asp | Ile<br>155 | Glu | Val | Gln | Asp | Pro<br>160 | Glu | Gly | Phe | |
| AAC | ATG | ATT | CTG | GGT | ACC | ATC | CTA | GCC | CAA | ATT | TGG | GTC | TTG | CTC | GCA | 644 |
| Asn | Met<br>165 | Ile | Leu | Gly | Thr | Ile<br>170 | Leu | Ala | Gln | Ile | Trp<br>175 | Val | Leu | Leu | Ala | |
| AAG | GCG | GTT | ACG | GCC | CCA | GAC | ACG | GCA | GCT | GAT | TCG | GAG | CTA | AGA | AGG | 692 |
| Lys<br>180 | Ala | Val | Thr | Ala | Pro<br>185 | Asp | Thr | Ala | Ala | Asp<br>190 | Ser | Glu | Leu | Arg | Arg<br>195 | |
| TGG | ATA | AAG | TAC | ACC | CAA | CAA | AGA | AGG | GTA | GTT | GGT | GAA | TTT | AGA | TTG | 740 |
| Trp | Ile | Lys | Tyr | Thr<br>200 | Gln | Gln | Arg | Arg | Val<br>205 | Val | Gly | Glu | Phe | Arg<br>210 | Leu | |
| GAG | AGA | AAA | TGG | TTG | GAT | GTG | GTG | AGG | AAC | AGG | ATT | GCC | GAG | GAC | CTC | 788 |
| Glu | Arg | Lys | Trp<br>215 | Leu | Asp | Val | Val | Arg<br>220 | Asn | Arg | Ile | Ala | Glu<br>225 | Asp | Leu | |
| TCC | TTA | CGC | CGA | TTC | ATG | GTC | GCT | CTA | ATC | CTG | GAT | ATC | AAG | AGA | ACA | 836 |
| Ser | Leu | Arg<br>230 | Arg | Phe | Met | Val | Ala<br>235 | Leu | Ile | Leu | Asp | Ile<br>240 | Lys | Arg | Thr | |
| CCC | GGA | AAC | AAA | CCC | AGG | ATT | GCT | GAA | ATG | ATA | TGT | GAC | ATT | GAT | ACA | 884 |
| Pro | Gly<br>245 | Asn | Lys | Pro | Arg | Ile<br>250 | Ala | Glu | Met | Ile | Cys<br>255 | Asp | Ile | Asp | Thr | |
| TAT | ATC | GTA | GAG | GCA | GGA | TTA | GCC | AGT | TTT | ATC | CTG | ACT | ATT | AAG | TTT | 932 |
| Tyr<br>260 | Ile | Val | Glu | Ala | Gly<br>265 | Leu | Ala | Ser | Phe | Ile<br>270 | Leu | Thr | Ile | Lys | Phe<br>275 | |
| GGG | ATA | GAA | ACT | ATG | TAT | CCT | GCT | CTT | GGA | CTG | CAT | GAA | TTT | GCT | GGT | 980 |
| Gly | Ile | Glu | Thr | Met<br>280 | Tyr | Pro | Ala | Leu | Gly<br>285 | Leu | His | Glu | Phe | Ala<br>290 | Gly | |
| GAG | TTA | TCC | ACA | CTT | GAG | TCC | TTG | ATG | AAC | CTT | TAC | CAG | CAA | ATG | GGG | 1028 |
| Glu | Leu | Ser | Thr<br>295 | Leu | Glu | Ser | Leu | Met<br>300 | Asn | Leu | Tyr | Gln | Gln<br>305 | Met | Gly | |
| GAA | ACT | GCA | CCC | TAC | ATG | GTA | AAC | CTG | GAG | AAC | TCA | ATT | CAG | AAC | AAG | 1076 |
| Glu | Thr | Ala<br>310 | Pro | Tyr | Met | Val | Asn<br>315 | Leu | Glu | Asn | Ser | Ile<br>320 | Gln | Asn | Lys | |
| TTC | AGT | GCA | GGA | TCA | TAC | CCT | CTG | CTC | TGG | AGC | TAT | GCC | ATG | GGA | GTA | 1124 |
| Phe | Ser<br>325 | Ala | Gly | Ser | Tyr | Pro<br>330 | Leu | Leu | Trp | Ser | Tyr<br>335 | Ala | Met | Gly | Val | |
| GGA | GTG | GAA | CTT | GAA | AAC | TCC | ATG | GGA | GGT | TTG | AAC | TTT | GGC | CGA | TCT | 1172 |
| Gly<br>340 | Val | Glu | Leu | Glu | Asn<br>345 | Ser | Met | Gly | Gly | Leu<br>350 | Asn | Phe | Gly | Arg | Ser<br>355 | |
| TAC | TTT | GAT | CCA | GCA | TAT | TTT | AGA | TTA | GGG | CAA | GAG | ATG | GTA | AGG | AGG | 1220 |
| Tyr | Phe | Asp | Pro | Ala<br>360 | Tyr | Phe | Arg | Leu | Gly<br>365 | Gln | Glu | Met | Val | Arg<br>370 | Arg | |
| TCA | GCT | GGA | AAG | GTC | AGT | TCC | ACA | TTG | GCA | TCT | GAA | CTC | GGT | ATC | ACT | 1268 |
| Ser | Ala | Gly | Lys<br>375 | Val | Ser | Ser | Thr | Leu<br>380 | Ala | Ser | Glu | Leu | Gly<br>385 | Ile | Thr | |

| | | | | | | | | | | | | | | | | |
|---|---|---|---|---|---|---|---|---|---|---|---|---|---|---|---|---|
| GCC | GAG | GAT | GCA | AGG | CTT | GTT | TCA | GAG | ATT | GCA | ATG | CAT | ACT | ACT | GAG | 1316 |
| Ala | Glu | Asp | Ala | Arg | Leu | Val | Ser | Glu | Ile | Ala | Met | His | Thr | Thr | Glu | |
| | | 390 | | | | | 395 | | | | | 400 | | | | |
| GAC | AAG | ATC | AGT | AGA | GCG | GTT | GGA | CCC | AGA | CAA | GCC | CAA | GTA | TCA | TTT | 1364 |
| Asp | Lys | Ile | Ser | Arg | Ala | Val | Gly | Pro | Arg | Gln | Ala | Gln | Val | Ser | Phe | |
| | 405 | | | | | 410 | | | | | 415 | | | | | |
| CTA | CAC | GGT | GAT | CAA | AGT | GAG | AAT | GAG | CTA | CCG | AGA | TTG | GGG | GGC | AAG | 1412 |
| Leu | His | Gly | Asp | Gln | Ser | Glu | Asn | Glu | Leu | Pro | Arg | Leu | Gly | Gly | Lys | |
| 420 | | | | | 425 | | | | | 430 | | | | | 435 | |
| GAA | GAT | AGG | AGG | GTC | AAA | CAG | AGT | CGA | GGA | GAA | GCC | AGG | GAG | AGC | TAC | 1460 |
| Glu | Asp | Arg | Arg | Val | Lys | Gln | Ser | Arg | Gly | Glu | Ala | Arg | Glu | Ser | Tyr | |
| | | | | 440 | | | | | 445 | | | | | 450 | | |
| AGA | GAA | ACC | GGG | CCC | AGC | AGA | GCA | AGT | GAT | GCG | AGA | GCT | GCC | CAT | CTT | 1508 |
| Arg | Glu | Thr | Gly | Pro | Ser | Arg | Ala | Ser | Asp | Ala | Arg | Ala | Ala | His | Leu | |
| | | | 455 | | | | | 460 | | | | | 465 | | | |
| CCA | ACC | GGC | ACA | CCC | CTA | GAC | ATT | GAC | ACT | GCA | TCG | GAG | TCC | AGC | CAA | 1556 |
| Pro | Thr | Gly | Thr | Pro | Leu | Asp | Ile | Asp | Thr | Ala | Ser | Glu | Ser | Ser | Gln | |
| | | 470 | | | | | 475 | | | | | 480 | | | | |
| GAT | CCG | CAG | GAC | AGT | CGA | AGG | TCA | GCT | GAC | GCC | CTG | CTT | AGG | CTG | CAA | 1604 |
| Asp | Pro | Gln | Asp | Ser | Arg | Arg | Ser | Ala | Asp | Ala | Leu | Leu | Arg | Leu | Gln | |
| | 485 | | | | | 490 | | | | | 495 | | | | | |
| GCC | ATG | GCA | GGA | ATC | TCG | GAA | GAA | CAA | GGC | TCA | GAC | ACG | GAC | ACC | CCT | 1652 |
| Ala | Met | Ala | Gly | Ile | Ser | Glu | Glu | Gln | Gly | Ser | Asp | Thr | Asp | Thr | Pro | |
| 500 | | | | | 505 | | | | | 510 | | | | | 515 | |
| ATA | GTG | TAC | AAT | GAC | AGA | AAT | CTT | CTA | GAC | TAGGTGCGAG | | | AGGCCGAGGA | | | 1702 |
| Ile | Val | Tyr | Asn | Asp | Arg | Asn | Leu | Leu | Asp | | | | | | | |
| | | | 520 | | | | | 525 | | | | | | | | |

| | | |
|---|---|---|
| CCAGAACAAC ATCCGCCTAC CCTCCATCAT TGTTATAAAA AACTTAGGAA CCAGGTCCAC | | 1762 |
| ACAGCCGCCA GCCCATCAAC CATCCACTCC CACGATTGGA GCCG ATG GCA GAA GAG | | 1818 |

| | | | | | | | | | | | | | | | | |
|---|---|---|---|---|---|---|---|---|---|---|---|---|---|---|---|---|
| | | | | | | | | | | | | Met | Ala | Glu | Glu | |
| | | | | | | | | | | | | 1 | | | | |
| CAG | GCA | CGC | CAT | GTC | AAA | AAC | GGA | CTG | GAA | TGC | ATC | CGG | GCT | CTC | AAG | 1866 |
| Gln | Ala | Arg | His | Val | Lys | Asn | Gly | Leu | Glu | Cys | Ile | Arg | Ala | Leu | Lys | |
| | 5 | | | | 10 | | | | | 15 | | | | | 20 | |
| GCC | GAG | CCC | ATC | GGC | TCA | CTG | GCC | ATC | GAG | GAA | GCT | ATG | GCA | GCA | TGG | 1914 |
| Ala | Glu | Pro | Ile | Gly | Ser | Leu | Ala | Ile | Glu | Glu | Ala | Met | Ala | Ala | Trp | |
| | | | | 25 | | | | | 30 | | | | | 35 | | |
| TCA | GAA | ATA | TCA | GAC | AAC | CCA | GGA | CAG | GAG | CGA | GCC | ACC | TGC | AGG | GAA | 1962 |
| Ser | Glu | Ile | Ser | Asp | Asn | Pro | Gly | Gln | Glu | Arg | Ala | Thr | Cys | Arg | Glu | |
| | | | 40 | | | | | 45 | | | | | 50 | | | |
| GAG | AAG | GCA | GGC | AGT | TCG | GGT | CTC | AGC | AAA | CCA | TGC | CTC | TCA | GCA | ATT | 2010 |
| Glu | Lys | Ala | Gly | Ser | Ser | Gly | Leu | Ser | Lys | Pro | Cys | Leu | Ser | Ala | Ile | |
| | | 55 | | | | | 60 | | | | | 65 | | | | |
| GGA | TCA | ACT | GAA | GGC | GGT | GCA | CCT | CGC | ATC | CGC | GGT | CAG | GGA | CCT | GGA | 2058 |
| Gly | Ser | Thr | Glu | Gly | Gly | Ala | Pro | Arg | Ile | Arg | Gly | Gln | Gly | Pro | Gly | |
| | 70 | | | | | 75 | | | | | 80 | | | | | |
| GAG | AGC | GAT | GAC | GAC | GCT | GAA | ACT | TTG | GGA | ATC | CCC | CCA | AGA | AAT | CTC | 2106 |
| Glu | Ser | Asp | Asp | Asp | Ala | Glu | Thr | Leu | Gly | Ile | Pro | Pro | Arg | Asn | Leu | |
| 85 | | | | | 90 | | | | | 95 | | | | | 100 | |
| CAG | GCA | TCA | AGC | ACT | GGG | TTA | CAG | TGT | TAT | TAT | GTT | TAT | GAT | CAC | AGC | 2154 |
| Gln | Ala | Ser | Ser | Thr | Gly | Leu | Gln | Cys | Tyr | Tyr | Val | Tyr | Asp | His | Ser | |
| | | | | 105 | | | | | 110 | | | | | 115 | | |
| GGT | GAA | GCG | GTT | AAG | GGA | ATC | CAA | GAT | GCT | GAC | TCT | ATC | ATG | GTT | CAA | 2202 |
| Gly | Glu | Ala | Val | Lys | Gly | Ile | Gln | Asp | Ala | Asp | Ser | Ile | Met | Val | Gln | |
| | | | 120 | | | | | 125 | | | | | 130 | | | |
| TCA | GGC | CTT | GAT | GGT | GAT | AGC | ACC | CTA | TCA | GGA | GGA | GAC | AAT | GAA | TCT | 2250 |
| Ser | Gly | Leu | Asp | Gly | Asp | Ser | Thr | Leu | Ser | Gly | Gly | Asp | Asn | Glu | Ser | |
| | | 135 | | | | | 140 | | | | | 145 | | | | |
| GAA | AAC | AGC | GAT | GTG | GAT | ATT | GGC | GAA | CCT | GAT | ACC | GAG | GGA | TAT | GCT | 2298 |

```
Glu  Asn  Ser  Asp  Val  Asp  Ile  Gly  Glu  Pro  Asp  Thr  Glu  Gly  Tyr  Ala
     150                      155                      160

ATC  ACT  GAC  CGG  GGA  TCT  GCT  CCC  ATC  TCT  ATG  GGG  TTC  AGG  GCT  TCT    2346
Ile  Thr  Asp  Arg  Gly  Ser  Ala  Pro  Ile  Ser  Met  Gly  Phe  Arg  Ala  Ser
165                      170                      175                      180

GAT  GTT  GAA  ACT  GCA  GAA  GGA  GGG  GAG  ATC  CAC  GAG  CTC  CTG  AGA  CTC    2394
Asp  Val  Glu  Thr  Ala  Glu  Gly  Gly  Glu  Ile  His  Glu  Leu  Leu  Arg  Leu
                    185                      190                      195

CAA  TCC  AGA  GGC  AAC  AAC  TTT  CCG  AAG  CTT  GGG  AAA  ACT  CTC  AAT  GTT    2442
Gln  Ser  Arg  Gly  Asn  Asn  Phe  Pro  Lys  Leu  Gly  Lys  Thr  Leu  Asn  Val
               200                      205                      210

CCT  CCG  CCC  CCG  GAC  CCC  GGT  AGG  GCC  AGC  ACT  TCC  GGG  ACA  CCC  ATT    2490
Pro  Pro  Pro  Pro  Asp  Pro  Gly  Arg  Ala  Ser  Thr  Ser  Gly  Thr  Pro  Ile
          215                      220                      225

AAA  AAG  GGC  ACA  GAG  CGC  AGA  TTA  GCC  TCA  TTT  GGA  ACG  GAG  ATC  GCG    2538
Lys  Lys  Gly  Thr  Glu  Arg  Arg  Leu  Ala  Ser  Phe  Gly  Thr  Glu  Ile  Ala
     230                      235                      240

TCT  TTA  TTG  ACA  GGT  GGT  GCA  ACC  CAA  TGT  GCT  CGA  AAG  TCA  CCC  TCG    2586
Ser  Leu  Leu  Thr  Gly  Gly  Ala  Thr  Gln  Cys  Ala  Arg  Lys  Ser  Pro  Ser
245                      250                      255                      260

GAA  CCA  TCA  GGG  CCA  GGT  GCA  CCT  GCG  GGG  AAT  GTC  CCC  GAG  TAT  GTG    2634
Glu  Pro  Ser  Gly  Pro  Gly  Ala  Pro  Ala  Gly  Asn  Val  Pro  Glu  Tyr  Val
                    265                      270                      275

AGC  AAT  GCC  GCA  CTG  ATA  CAG  GAG  TGG  ACA  CCC  GAA  TCT  GGT  ACC  ACA    2682
Ser  Asn  Ala  Ala  Leu  Ile  Gln  Glu  Trp  Thr  Pro  Glu  Ser  Gly  Thr  Thr
               280                      285                      290

ATC  TCC  CCG  AGA  TCC  CAG  AAT  AAT  GAA  GAA  GGG  GGA  GAC  TAT  TAT  GAT    2730
Ile  Ser  Pro  Arg  Ser  Gln  Asn  Asn  Glu  Glu  Gly  Gly  Asp  Tyr  Tyr  Asp
          295                      300                      305

GAT  GAG  CTG  TTC  TCT  GAT  GTC  CAA  GAT  ATT  AAA  ACA  GCC  TTG  GCC  AAA    2778
Asp  Glu  Leu  Phe  Ser  Asp  Val  Gln  Asp  Ile  Lys  Thr  Ala  Leu  Ala  Lys
     310                      315                      320

ATA  CAC  GAG  GAT  AAT  CAG  AAG  ATA  ATC  TCC  AAG  CTA  GAA  TCA  CTG  CTG    2826
Ile  His  Glu  Asp  Asn  Gln  Lys  Ile  Ile  Ser  Lys  Leu  Glu  Ser  Leu  Leu
325                      330                      335                      340

TTA  TTG  AAG  GGA  GAA  GTT  GAG  TCA  ATT  AAG  AAG  CAG  ATC  AAC  AGG  CAA    2874
Leu  Leu  Lys  Gly  Glu  Val  Glu  Ser  Ile  Lys  Lys  Gln  Ile  Asn  Arg  Gln
                    345                      350                      355

AAT  ATC  AGC  ATA  TCC  ACC  CTG  GAA  GGA  CAC  CTC  TCA  AGC  ATC  ATG  ATC    2922
Asn  Ile  Ser  Ile  Ser  Thr  Leu  Glu  Gly  His  Leu  Ser  Ser  Ile  Met  Ile
               360                      365                      370

GCC  ATT  CCT  GGA  CTT  GGG  AAG  GAT  CCC  AAC  GAC  CCC  ACT  GCA  GAT  GTC    2970
Ala  Ile  Pro  Gly  Leu  Gly  Lys  Asp  Pro  Asn  Asp  Pro  Thr  Ala  Asp  Val
          375                      380                      385

GAA  ATC  AAT  CCC  GAC  TTG  AAA  CCC  ATC  ATA  GGC  AGA  GAT  TCA  GGC  CGA    3018
Glu  Ile  Asn  Pro  Asp  Leu  Lys  Pro  Ile  Ile  Gly  Arg  Asp  Ser  Gly  Arg
     390                      395                      400

GCA  CTG  GCC  GAA  GTT  CTC  AAG  AAA  CCC  GTT  GCC  AGC  CGA  CAA  CTC  CAA    3066
Ala  Leu  Ala  Glu  Val  Leu  Lys  Lys  Pro  Val  Ala  Ser  Arg  Gln  Leu  Gln
405                      410                      415                      420

GGA  ATG  ACA  AAT  GGA  CGG  ACC  AGT  TCC  AGA  GGA  CAG  CTG  CTG  AAG  GAA    3114
Gly  Met  Thr  Asn  Gly  Arg  Thr  Ser  Ser  Arg  Gly  Gln  Leu  Leu  Lys  Glu
                    425                      430                      435

TTT  CAG  CCA  AAG  CCG  ATC  GGG  AAA  AAG  ATG  AGC  TCA  GCC  GTC  GGG  TTT    3162
Phe  Gln  Pro  Lys  Pro  Ile  Gly  Lys  Lys  Met  Ser  Ser  Ala  Val  Gly  Phe
               440                      445                      450

GTT  CCT  GAC  ACC  GGC  CCT  GCA  TCA  CGC  AGT  GTA  ATC  CGC  TCC  ATT  ATA    3210
Val  Pro  Asp  Thr  Gly  Pro  Ala  Ser  Arg  Ser  Val  Ile  Arg  Ser  Ile  Ile
          455                      460                      465

AAA  TCC  AGC  CGG  CTA  GAG  GAG  GAT  CGG  AAG  CGT  TAC  CTG  ATG  ACT  CTC    3258
```

```
Lys Ser Ser Arg Leu Glu Glu Asp Arg Lys Arg Tyr Leu Met Thr Leu
        470                 475                 480

CTT GAT GAT ATC AAA GGA GCC AAT GAT CTT GCC AAG TTC CAC CAG ATG    3306
Leu Asp Asp Ile Lys Gly Ala Asn Asp Leu Ala Lys Phe His Gln Met
485                 490                 495                 500

CTG ATG AAG ATA ATA ATG AAG TAGCTACAGC TCAACTTACC TGCCAACCCC       3357
Leu Met Lys Ile Ile Met Lys
                505

ATGCCAGTCG ACCCAACTAG TACAACCTAA ATCCATTATA AAAAACTTAG GAGCAAAGTG  3417

ATTGCCTCCC AAGTTCCACA ATG ACA GAG ATC TAC GAC TTC GAC AAG TCG      3467
                     Met Thr Glu Ile Tyr Asp Phe Asp Lys Ser
                      1               5                   10

GCA TGG GAC ATC AAA GGG TCG ATC GCT CCG ATA CAA CCC ACC ACC TAC    3515
Ala Trp Asp Ile Lys Gly Ser Ile Ala Pro Ile Gln Pro Thr Thr Tyr
            15                  20                  25

AGT GAT GGC AGG CTG GTG CCC CAG GTC AGA GTC ATA GAT CCT GGT CTA    3563
Ser Asp Gly Arg Leu Val Pro Gln Val Arg Val Ile Asp Pro Gly Leu
            30                  35                  40

GGC GAC AGG AAG GAT GAA TGC TTT ATG TAC ATG TCT CTG CTG GGG GTT    3611
Gly Asp Arg Lys Asp Glu Cys Phe Met Tyr Met Ser Leu Leu Gly Val
        45                  50                  55

GTT GAG GAC AGC GAT CCC CTA GGG CCT CCA ATC GGG CGA GCA TTT GGG    3659
Val Glu Asp Ser Asp Pro Leu Gly Pro Pro Ile Gly Arg Ala Phe Gly
60              65                  70

TCC CTG CCC TTA GGT GTT GGC AGA TCC ACA GCA AAG CCC GAA AAA CTC    3707
Ser Leu Pro Leu Gly Val Gly Arg Ser Thr Ala Lys Pro Glu Lys Leu
75              80                  85                  90

CTC AAA GAG GCC ACT GAG CTT GAC ATA GTT GTT AGA CGT ACA GCA GGG    3755
Leu Lys Glu Ala Thr Glu Leu Asp Ile Val Val Arg Arg Thr Ala Gly
                95                  100                 105

CTC AAT GAA AAA CTG GTG TTC TAC AAC AAC ACC CCA CTA ACT CTC CTC    3803
Leu Asn Glu Lys Leu Val Phe Tyr Asn Asn Thr Pro Leu Thr Leu Leu
            110                 115                 120

ACA CCT TGG AGA AAG GTC CTA ACA ACA GGG AGT GTC TTC AAC GCA AAC    3851
Thr Pro Trp Arg Lys Val Leu Thr Thr Gly Ser Val Phe Asn Ala Asn
        125                 130                 135

CAA GTG TGC AAT GCG GTT AAT CTG ATA CCG CTC GAT ACC CCG CAG AGG    3899
Gln Val Cys Asn Ala Val Asn Leu Ile Pro Leu Asp Thr Pro Gln Arg
140                 145                 150

TTC CGT GTT GTT TAT ATG AGC ATC ACC CGT CTT TCG GAT AAC GGG TAT    3947
Phe Arg Val Val Tyr Met Ser Ile Thr Arg Leu Ser Asp Asn Gly Tyr
155                 160                 165                 170

TAC ACC GTT CCT AGA AGA ATG CTG GAA TTC AGA TCG GTC AAT GCA GTG    3995
Tyr Thr Val Pro Arg Arg Met Leu Glu Phe Arg Ser Val Asn Ala Val
                175                 180                 185

GCC TTC AAC CTG CTG GTG ACC CTT AGG ATT GAC AAG GCG ATA GGC CCT    4043
Ala Phe Asn Leu Leu Val Thr Leu Arg Ile Asp Lys Ala Ile Gly Pro
            190                 195                 200

GGG AAG ATC ATC GAC AAT ACA GAG CAA CTT CCT GAG GCA ACA TTT ATG    4091
Gly Lys Ile Ile Asp Asn Thr Glu Gln Leu Pro Glu Ala Thr Phe Met
        205                 210                 215

GTC CAC ATC GGG AAC TTC AGG AGA AAG AAG AGT GAA GTC TAC TCT GCC    4139
Val His Ile Gly Asn Phe Arg Arg Lys Lys Ser Glu Val Tyr Ser Ala
220                 225                 230

GAT TAT TGC AAA ATG AAA ATC GAA AAG ATG GGC CTG GTT TTT GCA CTT    4187
Asp Tyr Cys Lys Met Lys Ile Glu Lys Met Gly Leu Val Phe Ala Leu
235                 240                 245                 250

GGT GGG ATA GGG GGC ACC AGT CTT CAC ATT AGA AGC ACA GGC AAA ATG    4235
Gly Gly Ile Gly Gly Thr Ser Leu His Ile Arg Ser Thr Gly Lys Met
```

```
                               255                             260                               265
AGC   AAG   ACT   CTC   CAT   GCA   CAA   CTC   GGG   TTC   AAG   AAG   ACC   TTA   TGT   TAC      4283
Ser   Lys   Thr   Leu   His   Ala   Gln   Leu   Gly   Phe   Lys   Lys   Thr   Leu   Cys   Tyr
                        270                           275                           280

CCG   CTG   ATG   GAT   ATC   AAT   GAA   GAC   CTT   AAT   CGA   TTA   CTC   TGG   AGG   AGC      4331
Pro   Leu   Met   Asp   Ile   Asn   Glu   Asp   Leu   Asn   Arg   Leu   Leu   Trp   Arg   Ser
            285                           290                           295

AGA   TGC   AAG   ATA   GTA   AGA   ATC   CAG   GCA   GTT   TTG   CAG   CCA   TCA   GTT   CCT      4379
Arg   Cys   Lys   Ile   Val   Arg   Ile   Gln   Ala   Val   Leu   Gln   Pro   Ser   Val   Pro
                  300                           305                           310

CAA   GAA   TTC   CGC   ATT   TAC   GAC   GAC   GTG   ATC   ATA   AAT   GAT   GAC   CAA   GGA      4427
Gln   Glu   Phe   Arg   Ile   Tyr   Asp   Asp   Val   Ile   Ile   Asn   Asp   Asp   Gln   Gly
315                           320                           325                           330

CTA   TTC   AAA   GTT   CTG   TAGACCGTAG   TGCCCAGCAA   TGCCCGAAAA   CGACCCCCCT                    4482
Leu   Phe   Lys   Val   Leu
                  335

CACAATGACA   GCCAGAAGGC   CCGGACAAAA   AAGCCCCCTC   CGAAAGACTC   CACTGACCAA                        4542

GCGAGAGGCC   AGCCAGCAGC   CGACGGCAAG   CACGAACACC   AGGCGGCCCC   AGCACAGAAC                        4602

AGCCCTGATA   CAAGGCCACC   ACCAGCCACC   CCAATCTGCA   TCCTCCTCGT   GGGACCCCCG                        4662

AGGACCAACC   CCCAAGGCTG   CCCCCGATCC   AAACCACCAA   CCGCATCCCC   ACCACCCCCG                        4722

GGAAAGAAAC   CCCCAGCAAT   TGGAAGGCCC   CTCCCCCTCT   TCCTCAACAC   AAGAACTCCA                        4782

CAACCGAACC   GCACAAGCGA   CCGAGGTGAC   CCAACCGCGC   GGCATCCGAC   TCCCTAGACA                        4842

GATCCTCTCT   CCCCGGCAAA   CTAAACAAAA   CTTAGGGCCA   AGGAACATAC   ACACCCAACA                        4902

GAACCCAGAC   CCCGGCCCAC   GGCGCCGCGC   CCCAACCCCC   CGACAACCAG   AGGGAGCCCC                        4962

CAACCAATCC   CGCCGGCTCC   CCCGGTGCCC   ACAGGCAGGG   ACACCAACCC   CGAACAGAC                         5022

CCAGCACCCA   ACCATCGACA   ATCCAAGACG   GGGGGGCCCC   CCCAAAAAAA   GGCCCCCAGG                        5082

GGCCGACAGC   CAGCACCGCG   AGGAAGCCCA   CCCACCCCAC   ACACGACCAC   GGCAACCAAA                        5142

CCAGAACCCA   GACCACCCTG   GCCACCAGCT   CCCAGACTCG   GCCATCACCC   CGCAGAAAGG                        5202

AAAGGCCACA   ACCCGCGCAC   CCCAGCCCCG   ATCCGGCGGG   GAGCCACCCA   ACCCGAACCA                        5262

GCACCCAAGA   GCGATCCCCG   AAGGACCCCC   GAACCGCAAA   GGACATCAGT   ATCCCACAGC                        5322

CTCTCCAAGT   CCCCCGGTCT   CCTCCTCTTC   TCGAAGGGAC   CAAAAGATCA   ATCCACCACA                        5382

CCCGACGACA   CTCAACTCCC   CACCCCTAAA   GGAGACACCG   GGAATCCCAG   AATCAAGACT                        5442

CATCCAATGT   CCATC   ATG   GGT   CTC   AAG   GTG   AAC   GTC   TCT   GCC   ATA   TTC   ATG         5493
                    Met   Gly   Leu   Lys   Val   Asn   Val   Ser   Ala   Ile   Phe   Met
                     1                5                             10

GCA   GTA   CTG   TTA   ACT   CTC   CAA   ACA   CCC   ACC   GGT   CAA   ATC   CAT   TGG   GGC      5541
Ala   Val   Leu   Leu   Thr   Leu   Gln   Thr   Pro   Thr   Gly   Gln   Ile   His   Trp   Gly
            15                            20                            25

AAT   CTC   TCT   AAG   ATA   GGG   GTG   GTA   GGA   ATA   GGA   AGT   GCA   AGC   TAC   AAA      5589
Asn   Leu   Ser   Lys   Ile   Gly   Val   Val   Gly   Ile   Gly   Ser   Ala   Ser   Tyr   Lys
                  30                            35                            40

GTT   ATG   ACT   CGT   TCC   AGC   CAT   CAA   TCA   TTA   GTC   ATA   AAA   TTA   ATG   CCC      5637
Val   Met   Thr   Arg   Ser   Ser   His   Gln   Ser   Leu   Val   Ile   Lys   Leu   Met   Pro
45                            50                            55                            60

AAT   ATA   ACT   CTC   CTC   AAT   AAC   TGC   ACG   AGG   GTA   GAG   ATT   GCA   GAA   TAC      5685
Asn   Ile   Thr   Leu   Leu   Asn   Asn   Cys   Thr   Arg   Val   Glu   Ile   Ala   Glu   Tyr
                        65                            70                            75

AGG   AGA   CTA   CTG   AGA   ACA   GTT   TTG   GAA   CCA   ATT   AGA   GAT   GCA   CTT   AAT      5733
Arg   Arg   Leu   Leu   Arg   Thr   Val   Leu   Glu   Pro   Ile   Arg   Asp   Ala   Leu   Asn
                  80                            85                            90

GCA   ATG   ACC   CAG   AAT   ATA   AGA   CCG   GTT   CAG   AGT   GTA   GCT   TCA   AGT   AGG      5781
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Ala | Met | Thr | Gln | Asn | Ile | Arg | Pro | Val | Gln | Ser | Val | Ala | Ser | Ser | Arg |      |
|     |     | 95  |     |     |     |     | 100 |     |     |     |     | 105 |     |     |     |      |
| AGA | CAC | AAG | AGA | TTT | GCG | GGA | GTA | GTC | CTG | GCA | GGT | GCG | GCC | CTA | GGC | 5829 |
| Arg | His | Lys | Arg | Phe | Ala | Gly | Val | Val | Leu | Ala | Gly | Ala | Ala | Leu | Gly |      |
|     | 110 |     |     |     | 115 |     |     |     |     | 120 |     |     |     |     |     |      |
| GTT | GCC | ACA | GCT | GCT | CAG | ATA | ACA | GCC | GGC | ATT | GCA | CTT | CAC | CAG | TCC | 5877 |
| Val | Ala | Thr | Ala | Ala | Gln | Ile | Thr | Ala | Gly | Ile | Ala | Leu | His | Gln | Ser |      |
| 125 |     |     |     | 130 |     |     |     |     | 135 |     |     |     |     | 140 |     |      |
| ATG | CTG | AAC | TCT | CAA | GCC | ATC | GAC | AAT | CTG | AGA | GCG | AGC | CTG | GAA | ACT | 5925 |
| Met | Leu | Asn | Ser | Gln | Ala | Ile | Asp | Asn | Leu | Arg | Ala | Ser | Leu | Glu | Thr |      |
|     |     |     |     | 145 |     |     |     |     | 150 |     |     |     |     | 155 |     |      |
| ACT | AAT | CAG | GCA | ATT | GAG | GCA | ATC | AGA | CAA | GCA | GGG | CAG | GAG | ATG | ATA | 5973 |
| Thr | Asn | Gln | Ala | Ile | Glu | Ala | Ile | Arg | Gln | Ala | Gly | Gln | Glu | Met | Ile |      |
|     |     |     | 160 |     |     |     |     | 165 |     |     |     |     | 170 |     |     |      |
| TTG | GCT | GTT | CAG | GGT | GTC | CAA | GAC | TAC | ATC | AAT | AAT | GAG | CTG | ATA | CCG | 6021 |
| Leu | Ala | Val | Gln | Gly | Val | Gln | Asp | Tyr | Ile | Asn | Asn | Glu | Leu | Ile | Pro |      |
|     |     | 175 |     |     |     |     | 180 |     |     |     |     | 185 |     |     |     |      |
| TCT | ATG | AAC | CAA | CTA | TCT | TGT | GAT | TTA | ATC | GGC | CAG | AAG | CTC | GGG | CTC | 6069 |
| Ser | Met | Asn | Gln | Leu | Ser | Cys | Asp | Leu | Ile | Gly | Gln | Lys | Leu | Gly | Leu |      |
|     | 190 |     |     |     |     | 195 |     |     |     |     | 200 |     |     |     |     |      |
| AAA | TTG | CTC | AGA | TAC | TAT | ACA | GAA | ATC | CTG | TCA | TTA | TTT | GGC | CCC | AGC | 6117 |
| Lys | Leu | Leu | Arg | Tyr | Tyr | Thr | Glu | Ile | Leu | Ser | Leu | Phe | Gly | Pro | Ser |      |
| 205 |     |     |     |     | 210 |     |     |     |     | 215 |     |     |     |     | 220 |      |
| TTA | CGG | GAC | CCC | ATA | TCT | GCG | GAG | ATA | TCT | ATC | CAG | GCT | TTG | AGC | TAT | 6165 |
| Leu | Arg | Asp | Pro | Ile | Ser | Ala | Glu | Ile | Ser | Ile | Gln | Ala | Leu | Ser | Tyr |      |
|     |     |     |     | 225 |     |     |     |     | 230 |     |     |     |     | 235 |     |      |
| GCG | CTT | GGA | GGA | GAC | ATC | AAT | AAG | GTG | TTA | GAA | AAG | CTC | GGA | TAC | AGT | 6213 |
| Ala | Leu | Gly | Gly | Asp | Ile | Asn | Lys | Val | Leu | Glu | Lys | Leu | Gly | Tyr | Ser |      |
|     |     |     | 240 |     |     |     |     | 245 |     |     |     |     | 250 |     |     |      |
| GGA | GGT | GAT | TTA | CTG | GGC | ATC | TTA | GAG | AGC | AGA | GGA | ATA | AAG | GCC | CGG | 6261 |
| Gly | Gly | Asp | Leu | Leu | Gly | Ile | Leu | Glu | Ser | Arg | Gly | Ile | Lys | Ala | Arg |      |
|     |     | 255 |     |     |     |     | 260 |     |     |     |     | 265 |     |     |     |      |
| ATA | ACT | CAC | GTC | GAC | ACA | GAG | TCC | TAC | TTA | ATT | GTC | CTC | AGT | ATA | GCC | 6309 |
| Ile | Thr | His | Val | Asp | Thr | Glu | Ser | Tyr | Leu | Ile | Val | Leu | Ser | Ile | Ala |      |
|     | 270 |     |     |     |     | 275 |     |     |     |     | 280 |     |     |     |     |      |
| TAT | CCG | ACG | CTG | TCC | GAG | ATT | AAG | GGG | GTG | ATT | GTC | CAC | CGG | CTA | GAG | 6357 |
| Tyr | Pro | Thr | Leu | Ser | Glu | Ile | Lys | Gly | Val | Ile | Val | His | Arg | Leu | Glu |      |
| 285 |     |     |     |     | 290 |     |     |     |     | 295 |     |     |     |     | 300 |      |
| GGG | GTC | TCG | TAC | AAC | ATA | GGC | TCT | CAA | GAG | TGG | TAT | ACC | ACT | GTG | CCC | 6405 |
| Gly | Val | Ser | Tyr | Asn | Ile | Gly | Ser | Gln | Glu | Trp | Tyr | Thr | Thr | Val | Pro |      |
|     |     |     |     | 305 |     |     |     |     | 310 |     |     |     |     | 315 |     |      |
| AAG | TAT | GTT | GCA | ACC | CAA | GGG | TAC | CTT | ATC | TCG | AAT | TTT | GAT | GAG | TCA | 6453 |
| Lys | Tyr | Val | Ala | Thr | Gln | Gly | Tyr | Leu | Ile | Ser | Asn | Phe | Asp | Glu | Ser |      |
|     |     |     | 320 |     |     |     |     | 325 |     |     |     |     | 330 |     |     |      |
| TCG | TGT | ACT | TTC | ATG | CCA | GAG | GGG | ACT | GTG | TGC | AGC | CAA | AAT | GCC | TTG | 6501 |
| Ser | Cys | Thr | Phe | Met | Pro | Glu | Gly | Thr | Val | Cys | Ser | Gln | Asn | Ala | Leu |      |
|     |     | 335 |     |     |     |     | 340 |     |     |     |     | 345 |     |     |     |      |
| TAC | CCG | ATG | AGT | CCT | CTG | CTC | CAA | GAA | TGC | CTC | CGG | GGG | TCC | ACC | AAG | 6549 |
| Tyr | Pro | Met | Ser | Pro | Leu | Leu | Gln | Glu | Cys | Leu | Arg | Gly | Ser | Thr | Lys |      |
|     | 350 |     |     |     |     | 355 |     |     |     |     | 360 |     |     |     |     |      |
| TCC | TGT | GCT | CGT | ACA | CTC | GTA | TCC | GGG | TCT | TTT | GGG | AAC | CGG | TTC | ATT | 6597 |
| Ser | Cys | Ala | Arg | Thr | Leu | Val | Ser | Gly | Ser | Phe | Gly | Asn | Arg | Phe | Ile |      |
| 365 |     |     |     |     | 370 |     |     |     |     | 375 |     |     |     |     | 380 |      |
| TTA | TCA | CAA | GGG | AAC | CTA | ATA | GCC | AAT | TGT | GCA | TCA | ATC | CTT | TGC | AAG | 6645 |
| Leu | Ser | Gln | Gly | Asn | Leu | Ile | Ala | Asn | Cys | Ala | Ser | Ile | Leu | Cys | Lys |      |
|     |     |     |     | 385 |     |     |     |     | 390 |     |     |     |     | 395 |     |      |
| TGT | TAC | ACA | ACA | GGA | ACG | ATC | ATT | AAT | CAA | GAC | CCT | GAC | AAG | ATC | CTA | 6693 |
| Cys | Tyr | Thr | Thr | Gly | Thr | Ile | Ile | Asn | Gln | Asp | Pro | Asp | Lys | Ile | Leu |      |
|     |     |     | 400 |     |     |     |     | 405 |     |     |     |     | 410 |     |     |      |
| ACA | TAC | ATT | GCT | GCC | GAT | CAC | TGC | CCG | GTA | GTC | GAG | GTG | AAC | GGC | GTG | 6741 |

|  |  |  |  |  |  |  |  |  |  |  |  |  |  |  |  |
|---|---|---|---|---|---|---|---|---|---|---|---|---|---|---|---|
| Thr | Tyr | Ile | Ala | Ala | Asp | His | Cys | Pro | Val | Val | Glu | Val | Asn | Gly | Val |
|  |  | 415 |  |  |  | 420 |  |  |  |  | 425 |  |  |  |  |

```
ACC ATC CAA GTC GGG AGC AGG AGG TAT CCA GAC GCT GTG TAC TTG CAC           6789
Thr Ile Gln Val Gly Ser Arg Arg Tyr Pro Asp Ala Val Tyr Leu His
    430             435             440

AGA ATT GAC CTC GGT CCT CCC ATA TTA TTG GAG AGG TTG GAC GTA GGG           6837
Arg Ile Asp Leu Gly Pro Pro Ile Leu Leu Glu Arg Leu Asp Val Gly
445             450             455             460

ACA AAT CTG GGG AAT GCA ATT GCT AAG TTG GAG GAT GCC AAG GAA TTG           6885
Thr Asn Leu Gly Asn Ala Ile Ala Lys Leu Glu Asp Ala Lys Glu Leu
                465             470             475

TTG GAG TCA TCG GAC CAG ATA TTG AGG AGT ATG AAA GGT TTA TCG AGC           6933
Leu Glu Ser Ser Asp Gln Ile Leu Arg Ser Met Lys Gly Leu Ser Ser
            480             485             490

ACT TGC ATA GTC TAC ATC CTG ATT GCA GTG TGT CTT GGA GGG TTG ATA           6981
Thr Cys Ile Val Tyr Ile Leu Ile Ala Val Cys Leu Gly Gly Leu Ile
        495             500             505

GGG ATC CCC GCT TTA ATA TGT TGC TGC AGG GGG CGT TGT AAC AAA AAG           7029
Gly Ile Pro Ala Leu Ile Cys Cys Cys Arg Gly Arg Cys Asn Lys Lys
    510             515             520

GGA GAA CAA GTT GGT ATG TCA AGA CCA GGC CTA AAG CCT GAT CTT ACG           7077
Gly Glu Gln Val Gly Met Ser Arg Pro Gly Leu Lys Pro Asp Leu Thr
525             530             535             540

GGA ACA TCA AAA TCC TAT GTA AGG TCG CTC TGATCCTCTA CAACTCTTGA             7127
Gly Thr Ser Lys Ser Tyr Val Arg Ser Leu
                545             550

AACACAAATG TCCCACAAGT CTCCTCTTCG TCATCAAGCA ACCACCGCAC CCAGCATCAA         7187

GCCCACCTGA AATTATCTCC GGCTTCCCTC TGGCCGAACA ATATCGGTAG TTAATTAAAA         7247

CTTAGGGTGC AAGATCATCC ACA ATG TCA CCA CAA CGA GAC CGG ATA AAT            7297
                         Met Ser Pro Gln Arg Asp Arg Ile Asn
                          1                  5

GCC TTC TAC AAA GAT AAC CCC CAT CCC AAG GGA AGT AGG ATA GTC ATT          7345
Ala Phe Tyr Lys Asp Asn Pro His Pro Lys Gly Ser Arg Ile Val Ile
 10              15              20                          25

AAC AGA GAA CAT CTT ATG ATT GAT AGA CCT TAT GTT TTG CTG GCT GTT          7393
Asn Arg Glu His Leu Met Ile Asp Arg Pro Tyr Val Leu Leu Ala Val
            30              35                          40

CTG TTT GTC ATG TTT CTG AGC TTG ATC GGG TTG CTA GCC ATT GCA GGC          7441
Leu Phe Val Met Phe Leu Ser Leu Ile Gly Leu Leu Ala Ile Ala Gly
         45              50              55

ATT AGA CTT CAT CGG GCA GCC ATC TAC ACC GCA GAG ATC CAT AAA AGC          7489
Ile Arg Leu His Arg Ala Ala Ile Tyr Thr Ala Glu Ile His Lys Ser
         60              65              70

CTC AGC ACC AAT CTA GAT GTA ACT AAC TCA ATC GAG CAT CAG GTC AAG          7537
Leu Ser Thr Asn Leu Asp Val Thr Asn Ser Ile Glu His Gln Val Lys
 75              80                          85

GAC GTG CTG ACA CCA CTC TTC AAA ATC ATC GGT GAT GAA GTG GGC CTG          7585
Asp Val Leu Thr Pro Leu Phe Lys Ile Ile Gly Asp Glu Val Gly Leu
 90              95              100                        105

AGG ACA CCT CAG AGA TTC ACT GAC CTA GTG AAA TTC ATC TCT GAC AAG          7633
Arg Thr Pro Gln Arg Phe Thr Asp Leu Val Lys Phe Ile Ser Asp Lys
             110             115                        120

ATT AAA TTC CTT AAT CCG GAT AGG GAG TAC GAC TTC AGA GAT CTC ACT          7681
Ile Lys Phe Leu Asn Pro Asp Arg Glu Tyr Asp Phe Arg Asp Leu Thr
             125             130                        135

TGG TGT ATG AAC CCG CCA GAG AGA ATC AAA TTG GAT TAT GAT CAA TAC          7729
Trp Cys Met Asn Pro Pro Glu Arg Ile Lys Leu Asp Tyr Asp Gln Tyr
             140             145             150
```

| | | | | | | | | | | | | | | | | |
|---|---|---|---|---|---|---|---|---|---|---|---|---|---|---|---|---|
| TGT | GCA | GAT | GTG | GCT | GCT | GAA | GAG | CTC | ATG | AAT | GCA | TTG | GTG | AAC | TCA | 7777 |
| Cys 155 | Ala | Asp | Val | Ala | Ala 160 | Glu | Glu | Leu | Met | Asn 165 | Ala | Leu | Val | Asn | Ser | |
| ACT | CTA | CTG | GAG | ACC | AGA | ACA | ACC | AAT | CAG | TTC | CTA | GCT | GTC | TCA | AAG | 7825 |
| Thr 170 | Leu | Leu | Glu | Thr | Arg 175 | Thr | Thr | Asn | Gln | Phe 180 | Leu | Ala | Val | Ser | Lys 185 | |
| GGA | AAC | TGC | TCA | GGG | CCC | ACT | ACA | ATC | AGA | GGT | CAA | TTC | TCA | AAC | ATG | 7873 |
| Gly | Asn | Cys | Ser | Gly 190 | Pro | Thr | Thr | Ile | Arg 195 | Gly | Gln | Phe | Ser | Asn | Met 200 | |
| TCG | CTG | TCC | CTG | TTA | GAC | TTG | TAT | TTA | GGT | CGA | GGT | TAC | AAT | GTG | TCA | 7921 |
| Ser | Leu | Ser | Leu 205 | Leu | Asp | Leu | Tyr | Leu 210 | Gly | Arg | Gly | Tyr | Asn 215 | Val | Ser | |
| TCT | ATA | GTC | ACT | ATG | ACA | TCC | CAG | GGA | ATG | TAT | GGG | GGA | ACT | TAC | CTA | 7969 |
| Ser | Ile | Val 220 | Thr | Met | Thr | Ser | Gln 225 | Gly | Met | Tyr | Gly | Gly 230 | Thr | Tyr | Leu | |
| GTG | GAA | AAG | CCT | AAT | CTG | AGC | AGC | AAA | AGG | TCA | GAG | TTG | TCA | CAA | CTG | 8017 |
| Val | Glu 235 | Lys | Pro | Asn | Leu | Ser 240 | Ser | Lys | Arg | Ser | Glu 245 | Leu | Ser | Gln | Leu | |
| AGC | ATG | TAC | CGA | GTG | TTT | GAA | GTA | GGT | GTT | ATC | AGA | AAT | CCG | GGT | TTG | 8065 |
| Ser 250 | Met | Tyr | Arg | Val | Phe 255 | Glu | Val | Gly | Val | Ile 260 | Arg | Asn | Pro | Gly | Leu 265 | |
| GGG | GCT | CCG | GTG | TTC | CAT | ATG | ACA | AAC | TAT | CTT | GAG | CAA | CCA | GTC | AGT | 8113 |
| Gly | Ala | Pro | Val | Phe 270 | His | Met | Thr | Asn | Tyr 275 | Leu | Glu | Gln | Pro | Val 280 | Ser | |
| AAT | GAT | CTC | AGC | AAC | TGT | ATG | GTG | GCT | TTG | GGG | GAG | CTC | AAA | CTC | GCA | 8161 |
| Asn | Asp | Leu | Ser 285 | Asn | Cys | Met | Val | Ala 290 | Leu | Gly | Glu | Leu | Lys 295 | Leu | Ala | |
| GCC | CTT | TGT | CAC | CGG | GAA | GAT | TCT | ATC | ACA | ATT | CCC | TAT | CAG | GGA | TCA | 8209 |
| Ala | Leu | Cys 300 | His | Arg | Glu | Asp | Ser 305 | Ile | Thr | Ile | Pro | Tyr 310 | Gln | Gly | Ser | |
| GGG | AAA | GGT | GTC | AGC | TTC | CAG | CTC | GTC | AAG | CTA | GGT | GTC | TGG | AAA | TCC | 8257 |
| Gly | Lys | Gly 315 | Val | Ser | Phe | Gln | Leu 320 | Val | Lys | Leu | Gly | Val 325 | Trp | Lys | Ser | |
| CCA | ACC | GAC | ATG | CAA | TCC | TGG | GTC | ACC | TTA | TCA | ACG | GAT | GAT | CCA | GTG | 8305 |
| Pro 330 | Thr | Asp | Met | Gln | Ser 335 | Trp | Val | Thr | Leu | Ser 340 | Thr | Asp | Asp | Pro | Val 345 | |
| ATA | GAC | AGG | CTT | TAC | CTC | TCA | TCT | CAC | AGA | GGT | GTT | ATC | GCT | GAC | AAT | 8353 |
| Ile | Asp | Arg | Leu | Tyr 350 | Leu | Ser | Ser | His | Arg 355 | Gly | Val | Ile | Ala | Asp 360 | Asn | |
| CAA | GCA | AAA | TGG | GCT | GTC | CCG | ACA | ACA | CGA | ACA | GAT | GAC | AAG | TTG | CGA | 8401 |
| Gln | Ala | Lys | Trp 365 | Ala | Val | Pro | Thr | Thr 370 | Arg | Thr | Asp | Asp | Lys 375 | Leu | Arg | |
| ATG | GAG | ACA | TGC | TTC | CAA | CAG | GCG | TGT | AAG | GGT | AAA | ATC | CAA | GCA | CTC | 8449 |
| Met | Glu | Thr 380 | Cys | Phe | Gln | Gln | Ala 385 | Cys | Lys | Gly | Lys | Ile 390 | Gln | Ala | Leu | |
| TGC | GAG | AAT | CCC | GAG | TGG | GCA | CCA | TTG | AAG | GAT | AAC | AGG | ATT | CCT | TCA | 8497 |
| Cys 395 | Glu | Asn | Pro | Glu | Trp 400 | Ala | Pro | Leu | Lys | Asp 405 | Asn | Arg | Ile | Pro | Ser | |
| TAC | GGG | GTC | TTG | TCT | GTT | GAT | CTG | AGT | CTG | ACA | GTT | GAG | CTT | AAA | ATC | 8545 |
| Tyr 410 | Gly | Val | Leu | Ser | Val 415 | Asp | Leu | Ser | Leu | Thr 420 | Val | Glu | Leu | Lys | Ile 425 | |
| AAA | ATT | GCT | TCG | GGA | TTC | GGG | CCA | TTG | ATC | ACA | CAC | GGT | TCA | GGG | ATG | 8593 |
| Lys | Ile | Ala | Ser | Gly 430 | Phe | Gly | Pro | Leu | Ile 435 | Thr | His | Gly | Ser | Gly 440 | Met | |
| GAC | CTA | TAC | AAA | TCC | AAC | CAC | AAC | AAT | GTG | TAT | TGG | CTG | ACT | ATC | CCA | 8641 |
| Asp | Leu | Tyr | Lys 445 | Ser | Asn | His | Asn | Asn 450 | Val | Tyr | Trp | Leu | Thr 455 | Ile | Pro | |
| CCA | ATG | AAG | AAC | CTA | GCC | TTA | GGT | GTA | ATC | AAC | ACA | TTG | GAG | TGG | ATA | 8689 |
| Pro | Met | Lys | Asn 460 | Leu | Ala | Leu | Gly | Val 465 | Ile | Asn | Thr | Leu | Glu 470 | Trp | Ile | |

-continued

| | | | | | | | | | | | | | | | | |
|---|---|---|---|---|---|---|---|---|---|---|---|---|---|---|---|---|
| CCG | AGA | TTC | AAG | GTT | AGT | CCC | TAC | CTC | TTC | AAT | GTC | CCA | ATT | AAG | GAA | 8737 |
| Pro | Arg 475 | Phe | Lys | Val | Ser | Pro 480 | Tyr | Leu | Phe | Asn | Val 485 | Pro | Ile | Lys | Glu | |
| GCA | GGC | GAA | GAC | TGC | CAT | GCC | CCA | ACA | TAC | CTA | CCT | GCG | GAG | GTG | GAT | 8785 |
| Ala 490 | Gly | Glu | Asp | Cys | His 495 | Ala | Pro | Thr | Tyr | Leu 500 | Pro | Ala | Glu | Val | Asp 505 | |
| GGT | GAT | GTC | AAA | CTC | AGT | TCC | AAT | CTG | GTG | ATT | CTA | CCT | GGT | CAA | GAT | 8833 |
| Gly | Asp | Val | Lys | Leu 510 | Ser | Ser | Asn | Leu | Val 515 | Ile | Leu | Pro | Gly | Gln 520 | Asp | |
| CTC | CAA | TAT | GTT | TTG | GCA | ACC | TAC | GAT | ACT | TCC | AGG | GTT | GAA | CAT | GCT | 8881 |
| Leu | Gln | Tyr | Val 525 | Leu | Ala | Thr | Tyr | Asp 530 | Thr | Ser | Arg | Val | Glu 535 | His | Ala | |
| GTG | GTT | TAT | TAC | GTT | TAC | AGC | CCA | AGC | CGC | TCA | TTT | TCT | TAC | TTT | TAT | 8929 |
| Val | Val | Tyr 540 | Tyr | Val | Tyr | Ser | Pro 545 | Ser | Arg | Ser | Phe | Ser 550 | Tyr | Phe | Tyr | |
| CCT | TTT | AGG | TTG | CCT | ATA | AAG | GGG | GTC | CCC | ATC | GAA | TTA | CAA | GTG | GAA | 8977 |
| Pro | Phe 555 | Arg | Leu | Pro | Ile | Lys 560 | Gly | Val | Pro | Ile | Glu 565 | Leu | Gln | Val | Glu | |
| TGC | TTC | ACA | TGG | GAC | CAA | AAA | CTC | TGG | TGC | CGT | CAC | TTC | TGT | GTG | CTT | 9025 |
| Cys 570 | Phe | Thr | Trp | Asp | Gln 575 | Lys | Leu | Trp | Cys | Arg 580 | His | Phe | Cys | Val | Leu 585 | |
| GCG | GAC | TCA | GAA | TCT | GGT | GGA | CAT | ATC | ACT | CAC | TCT | GGG | ATG | GTG | GGC | 9073 |
| Ala | Asp | Ser | Glu | Ser 590 | Gly | Gly | His | Ile | Thr 595 | His | Ser | Gly | Met | Val 600 | Gly | |
| ATG | GGA | GTC | AGC | TGC | ACA | GTC | ACC | CGG | GAA | GAT | GGA | ACC | AAT | CGC | AGA | 9121 |
| Met | Gly | Val | Ser 605 | Cys | Thr | Val | Thr | Arg 610 | Glu | Asp | Gly | Thr | Asn 615 | Arg | Arg | |

TAGGGCTGCT AGTGAACTAA TCTCATGATG TCACCCAGAC ATCAGGCATA CCCACTAGTG    9181
TGAAATAGAC ATCAGAATTA AGAAAAACGT AGGGTCCAAG TGGTTCCCCG TT ATG        9236
                                                                    Met
                                                                      1

| | | | | | | | | | | | | | | | | |
|---|---|---|---|---|---|---|---|---|---|---|---|---|---|---|---|---|
| GAC | TCG | CTA | TCT | GTC | AAC | CAG | ATC | TTA | TAC | CCT | GAA | GTT | CAC | CTA | GAT | 9284 |
| Asp | Ser | Leu | Ser 5 | Val | Asn | Gln | Ile | Leu 10 | Tyr | Pro | Glu | Val | His 15 | Leu | Asp | |
| AGC | CCG | ATA | GTT | ACC | AAT | AAG | ATA | GTA | GCC | ATC | CTG | GAG | TAT | GCT | CGA | 9332 |
| Ser | Pro | Ile 20 | Val | Thr | Asn | Lys | Ile 25 | Val | Ala | Ile | Leu | Glu 30 | Tyr | Ala | Arg | |
| GTT | CCT | CAC | GCT | TAC | AGC | CTG | GAG | GAC | CCT | ACA | CTG | TGT | CAG | AAC | ATC | 9380 |
| Val | Pro | His 35 | Ala | Tyr | Ser | Leu | Glu 40 | Asp | Pro | Thr | Leu | Cys 45 | Gln | Asn | Ile | |
| AAG | CAC | CGC | CTA | AAA | AAC | GGA | TTT | TCC | AAC | CAA | ATG | ATT | ATA | AAC | AAT | 9428 |
| Lys 50 | His | Arg | Leu | Lys | Asn 55 | Gly | Phe | Ser | Asn | Gln 60 | Met | Ile | Ile | Asn | Asn 65 | |
| GTG | GAA | GTT | GGG | AAT | GTC | ATC | AAG | TCC | AAG | CTT | AGG | AGT | TAT | CCG | GCC | 9476 |
| Val | Glu | Val | Gly | Asn 70 | Val | Ile | Lys | Ser | Lys 75 | Leu | Arg | Ser | Tyr | Pro 80 | Ala | |
| CAC | TCT | CAT | ATT | CCA | TAT | CCA | AAT | TGT | AAT | CAG | GAT | TTA | TTT | AAC | ATA | 9524 |
| His | Ser | His | Ile 85 | Pro | Tyr | Pro | Asn | Cys 90 | Asn | Gln | Asp | Leu | Phe 95 | Asn | Ile | |
| GAA | GAC | AAA | GAG | TCA | ACG | AGG | AAG | ATC | CGT | GAA | CTC | CTC | AAA | AAG | GGG | 9572 |
| Glu | Asp | Lys 100 | Glu | Ser | Thr | Arg | Lys 105 | Ile | Arg | Glu | Leu | Leu 110 | Lys | Lys | Gly | |
| AAT | TCG | CTG | TAC | TCC | AAA | GTC | AGT | GAT | AAG | GTT | TTC | CAA | TGC | TTA | AGG | 9620 |
| Asn | Ser | Leu | Tyr | Ser 115 | Lys | Val | Ser | Asp | Lys 120 | Val | Phe | Gln | Cys | Leu 125 | Arg | |
| GAC | ACT | AAC | TCA | CGG | CTT | GGC | CTA | GGC | TCC | GAA | TTG | AGG | GAG | GAC | ATC | 9668 |
| Asp | Thr | Asn | Ser 130 | Arg | Leu | Gly | Leu | Gly 135 | Ser | Glu | Leu | Arg | Glu 140 | Asp | Ile 145 | |

| | | | | | | | | | | | | | | | | |
|---|---|---|---|---|---|---|---|---|---|---|---|---|---|---|---|---|
| AAG | GAG | AAA | GTT | ATT | AAC | TTG | GGA | GTT | TAC | ATG | CAC | AGC | TCC | CAG | TGG | 9716 |
| Lys | Glu | Lys | Val | Ile | Asn | Leu | Gly | Val | Tyr | Met | His | Ser | Ser | Gln | Trp | |
| | | | | 150 | | | | 155 | | | | | | 160 | | |
| TTT | GAG | CCA | TTT | CTG | TTT | TGG | TTT | ACA | GTC | AAG | ACT | GAG | ATG | AGG | TCA | 9764 |
| Phe | Glu | Pro | Phe | Leu | Phe | Trp | Phe | Thr | Val | Lys | Thr | Glu | Met | Arg | Ser | |
| | | | 165 | | | | | 170 | | | | | 175 | | | |
| GTG | ATT | AAA | TCA | CAA | ACC | CAT | ACT | TGC | CAT | AGG | AGG | AGA | CAC | ACA | CCT | 9812 |
| Val | Ile | Lys | Ser | Gln | Thr | His | Thr | Cys | His | Arg | Arg | Arg | His | Thr | Pro | |
| | | 180 | | | | | 185 | | | | | 190 | | | | |
| GTA | TTC | TTC | ACT | GGT | AGT | TCA | GTT | GAG | TTG | CTA | ATC | TCT | CGT | GAC | CTT | 9860 |
| Val | Phe | Phe | Thr | Gly | Ser | Ser | Val | Glu | Leu | Leu | Ile | Ser | Arg | Asp | Leu | |
| | 195 | | | | | 200 | | | | | 205 | | | | | |
| GTT | GCT | ATA | ATC | AGT | AAA | GAG | TCT | CAA | CAT | GTA | TAT | TAC | CTG | ACA | TTT | 9908 |
| Val | Ala | Ile | Ile | Ser | Lys | Glu | Ser | Gln | His | Val | Tyr | Tyr | Leu | Thr | Phe | |
| 210 | | | | | 215 | | | | | 220 | | | | | 225 | |
| GAA | CTG | GTT | TTG | ATG | TAT | TGT | GAT | GTC | ATA | GAG | GGG | AGG | TTA | ATG | ACA | 9956 |
| Glu | Leu | Val | Leu | Met | Tyr | Cys | Asp | Val | Ile | Glu | Gly | Arg | Leu | Met | Thr | |
| | | | | 230 | | | | 235 | | | | | 240 | | | |
| GAG | ACC | GCT | ATG | ACT | ATT | GAT | GCT | AGG | TAT | ACA | GAG | CTT | CTA | GGA | AGA | 10004 |
| Glu | Thr | Ala | Met | Thr | Ile | Asp | Ala | Arg | Tyr | Thr | Glu | Leu | Leu | Gly | Arg | |
| | | | 245 | | | | 250 | | | | | 255 | | | | |
| GTC | AGA | TAC | ATG | TGG | AAA | CTG | ATA | GAT | GGT | TTC | TTC | CCT | GCA | CTC | GGG | 10052 |
| Val | Arg | Tyr | Met | Trp | Lys | Leu | Ile | Asp | Gly | Phe | Phe | Pro | Ala | Leu | Gly | |
| | | 260 | | | | | 265 | | | | | 270 | | | | |
| AAT | CCA | ACT | TAT | CAA | ATT | GTA | GCC | ATG | CTG | GAG | CCT | CTT | TCA | CTT | GCT | 10100 |
| Asn | Pro | Thr | Tyr | Gln | Ile | Val | Ala | Met | Leu | Glu | Pro | Leu | Ser | Leu | Ala | |
| | 275 | | | | | 280 | | | | | 285 | | | | | |
| TAC | CTG | CAG | CTG | AGG | GAT | ATA | ACA | GTA | GAA | CTC | AGA | GGT | GCT | TTC | CTT | 10148 |
| Tyr | Leu | Gln | Leu | Arg | Asp | Ile | Thr | Val | Glu | Leu | Arg | Gly | Ala | Phe | Leu | |
| 290 | | | | | 295 | | | | | 300 | | | | | 305 | |
| AAC | CAC | TGC | TTT | ACT | GAA | ATA | CAT | GAT | GTT | CTT | GAC | CAA | AAC | GGG | TTT | 10196 |
| Asn | His | Cys | Phe | Thr | Glu | Ile | His | Asp | Val | Leu | Asp | Gln | Asn | Gly | Phe | |
| | | | 310 | | | | 315 | | | | | 320 | | | | |
| TCT | GAT | GAA | GGT | ACT | TAT | CAT | GAG | TTA | ATT | GAA | GCT | CTA | GAT | TAC | ATT | 10244 |
| Ser | Asp | Glu | Gly | Thr | Tyr | His | Glu | Leu | Ile | Glu | Ala | Leu | Asp | Tyr | Ile | |
| | | | 325 | | | | 330 | | | | | 335 | | | | |
| TTC | ATA | ACT | GAT | GAC | ATA | CAT | CTG | ACA | GGG | GAG | ATT | TTC | TCA | TTT | TTC | 10292 |
| Phe | Ile | Thr | Asp | Asp | Ile | His | Leu | Thr | Gly | Glu | Ile | Phe | Ser | Phe | Phe | |
| | | 340 | | | | | 345 | | | | | 350 | | | | |
| AGA | AGT | TTC | GGC | CAC | CCC | AGA | CTT | GAA | GCA | GTA | ACG | GCT | GCT | GAA | AAT | 10340 |
| Arg | Ser | Phe | Gly | His | Pro | Arg | Leu | Glu | Ala | Val | Thr | Ala | Ala | Glu | Asn | |
| 355 | | | | | 360 | | | | | 365 | | | | | | |
| GTT | AGG | AAA | TAC | ATG | AAT | CAG | CCT | AAA | GTC | ATT | GTG | TAT | GAG | ACT | CTG | 10388 |
| Val | Arg | Lys | Tyr | Met | Asn | Gln | Pro | Lys | Val | Ile | Val | Tyr | Glu | Thr | Leu | |
| 370 | | | | | 375 | | | | | 380 | | | | | 385 | |
| ATG | AAA | GGT | CAT | GCC | ATA | TTT | TGT | GGA | ATC | ATA | ATC | AAC | GGC | TAT | CGT | 10436 |
| Met | Lys | Gly | His | Ala | Ile | Phe | Cys | Gly | Ile | Ile | Ile | Asn | Gly | Tyr | Arg | |
| | | | | 390 | | | | 395 | | | | | 400 | | | |
| GAC | AGG | CAC | GGA | GGC | AGT | TGG | CCA | CCG | CTG | ACC | CTC | CCC | CTG | CAT | GCT | 10484 |
| Asp | Arg | His | Gly | Gly | Ser | Trp | Pro | Pro | Leu | Thr | Leu | Pro | Leu | His | Ala | |
| | | | 405 | | | | 410 | | | | | 415 | | | | |
| GCA | GAC | ACA | ATC | CGG | AAT | GCT | CAA | GCT | TCA | GGT | GAA | GGG | TTA | ACA | CAT | 10532 |
| Ala | Asp | Thr | Ile | Arg | Asn | Ala | Gln | Ala | Ser | Gly | Glu | Gly | Leu | Thr | His | |
| | | 420 | | | | | 425 | | | | | 430 | | | | |
| GAG | CAG | TGC | GTT | GAT | AAC | TGG | AAA | TCT | TTT | GCT | GGA | GTG | AAA | TTT | GGC | 10580 |
| Glu | Gln | Cys | Val | Asp | Asn | Trp | Lys | Ser | Phe | Ala | Gly | Val | Lys | Phe | Gly | |
| | | 435 | | | | | 440 | | | | | 445 | | | | |
| TGC | TTT | ATG | CCT | CTT | AGC | CTG | GAT | AGT | GAT | CTG | ACA | ATG | TAC | CTA | AAG | 10628 |
| Cys | Phe | Met | Pro | Leu | Ser | Leu | Asp | Ser | Asp | Leu | Thr | Met | Tyr | Leu | Lys | |
| 450 | | | | | 455 | | | | | 460 | | | | | 465 | |

| | | | | | | | | | | | | | | | | |
|---|---|---|---|---|---|---|---|---|---|---|---|---|---|---|---|---|
| GAC | AAG | GCA | CTT | GCT | GCT | CTC | CAA | AGG | GAA | TGG | GAT | TCA | GTT | TAC | CCG | 10676 |
| Asp | Lys | Ala | Leu | Ala | Ala | Leu | Gln | Arg | Glu | Trp | Asp | Ser | Val | Tyr | Pro | |
| | | | 470 | | | | | 475 | | | | | | 480 | | |
| AAA | GAG | TTC | CTG | CGT | TAC | GAC | CCT | CCC | AAG | GGA | ACC | GGG | TCA | CGG | AGG | 10724 |
| Lys | Glu | Phe | Leu | Arg | Tyr | Asp | Pro | Pro | Lys | Gly | Thr | Gly | Ser | Arg | Arg | |
| | | | 485 | | | | | 490 | | | | | 495 | | | |
| CTT | GTA | GAT | GTT | TTC | CTT | AAT | GAT | TCG | AGC | TTT | GAC | CCA | TAT | GAT | GTG | 10772 |
| Leu | Val | Asp | Val | Phe | Leu | Asn | Asp | Ser | Ser | Phe | Asp | Pro | Tyr | Asp | Val | |
| | | 500 | | | | | 505 | | | | | 510 | | | | |
| ATA | ATG | TAT | GTT | GTA | AGT | GGA | GCT | TAC | CTC | CAT | GAC | CCT | GAG | TTC | AAC | 10820 |
| Ile | Met | Tyr | Val | Val | Ser | Gly | Ala | Tyr | Leu | His | Asp | Pro | Glu | Phe | Asn | |
| | | 515 | | | | | 520 | | | | | 525 | | | | |
| CTG | TCT | TAC | AGC | CTG | AAA | GAA | AAG | GAG | ATC | AAG | GAA | ACA | GGT | AGA | CTT | 10868 |
| Leu | Ser | Tyr | Ser | Leu | Lys | Glu | Lys | Glu | Ile | Lys | Glu | Thr | Gly | Arg | Leu | |
| 530 | | | | | 535 | | | | | 540 | | | | | 545 | |
| TTT | GCT | AAA | ATG | ACT | TAC | AAA | ATG | AGG | GCA | TGC | CAA | GTG | ATT | GCT | GAA | 10916 |
| Phe | Ala | Lys | Met | Thr | Tyr | Lys | Met | Arg | Ala | Cys | Gln | Val | Ile | Ala | Glu | |
| | | | | 550 | | | | | 555 | | | | | 560 | | |
| AAT | CTA | ATC | TCA | AAC | GGG | ATT | GGC | AAA | TAT | TTT | AAG | GAC | AAT | GGG | ATG | 10964 |
| Asn | Leu | Ile | Ser | Asn | Gly | Ile | Gly | Lys | Tyr | Phe | Lys | Asp | Asn | Gly | Met | |
| | | | 565 | | | | | 570 | | | | | 575 | | | |
| GCC | AAG | GAT | GAG | CAC | GAT | TTG | ACT | AAG | GCA | CTC | CAC | ACT | CTA | GCT | GTC | 11012 |
| Ala | Lys | Asp | Glu | His | Asp | Leu | Thr | Lys | Ala | Leu | His | Thr | Leu | Ala | Val | |
| | | | 580 | | | | | 585 | | | | | 590 | | | |
| TCA | GGA | GTC | CCC | AAA | GAT | CTC | AAA | GAA | AGT | CAC | AGG | GGG | GGG | CCA | GTC | 11060 |
| Ser | Gly | Val | Pro | Lys | Asp | Leu | Lys | Glu | Ser | His | Arg | Gly | Gly | Pro | Val | |
| | 595 | | | | | 600 | | | | | 605 | | | | | |
| TTA | AAA | ACC | TAC | TCC | CGA | AGC | CCA | GTC | CAC | ACA | AGT | ACC | AGG | AAC | GTG | 11108 |
| Leu | Lys | Thr | Tyr | Ser | Arg | Ser | Pro | Val | His | Thr | Ser | Thr | Arg | Asn | Val | |
| 610 | | | | | 615 | | | | | 620 | | | | | 625 | |
| AGA | GCA | GCA | AAA | GGG | TTT | ATA | GGG | TTC | CCT | CAA | GTA | ATT | CGG | CAG | GAC | 11156 |
| Arg | Ala | Ala | Lys | Gly | Phe | Ile | Gly | Phe | Pro | Gln | Val | Ile | Arg | Gln | Asp | |
| | | | | 630 | | | | | 635 | | | | | 640 | | |
| CAA | GAC | ACT | GAT | CAT | CCG | GAG | AAT | ATG | GAA | GCT | TAC | GAG | ACA | GTC | AGT | 11204 |
| Gln | Asp | Thr | Asp | His | Pro | Glu | Asn | Met | Glu | Ala | Tyr | Glu | Thr | Val | Ser | |
| | | | 645 | | | | | 650 | | | | | 655 | | | |
| GCA | TTT | ATC | ACG | ACT | GAT | CTC | AAG | AAG | TAC | TGC | CTT | AAT | TGG | AGA | TAT | 11252 |
| Ala | Phe | Ile | Thr | Thr | Asp | Leu | Lys | Lys | Tyr | Cys | Leu | Asn | Trp | Arg | Tyr | |
| | | | 660 | | | | | 665 | | | | | 670 | | | |
| GAG | ACC | ATC | AGC | TTG | TTT | GCA | CAG | AGG | CTA | AAT | GAG | ATT | TAC | GGA | TTG | 11300 |
| Glu | Thr | Ile | Ser | Leu | Phe | Ala | Gln | Arg | Leu | Asn | Glu | Ile | Tyr | Gly | Leu | |
| | 675 | | | | | 680 | | | | | 685 | | | | | |
| CCC | TCA | TTT | TTC | CAG | TGG | CTG | CAT | AAG | AGG | CTT | GAG | ACC | TCT | GTC | CTG | 11348 |
| Pro | Ser | Phe | Phe | Gln | Trp | Leu | His | Lys | Arg | Leu | Glu | Thr | Ser | Val | Leu | |
| 690 | | | | 695 | | | | | 700 | | | | | 705 | | |
| TAT | GTA | AGT | GAC | CCT | CAT | TGC | CCC | CCC | GAC | CTT | GAC | GCC | CAT | ATC | CCG | 11396 |
| Tyr | Val | Ser | Asp | Pro | His | Cys | Pro | Pro | Asp | Leu | Asp | Ala | His | Ile | Pro | |
| | | | | 710 | | | | | 715 | | | | | 720 | | |
| TTA | TAT | AAA | GTC | CCC | AAT | GAT | CAA | ATC | TTC | ATT | AAG | TAC | CCT | ATG | GGA | 11444 |
| Leu | Tyr | Lys | Val | Pro | Asn | Asp | Gln | Ile | Phe | Ile | Lys | Tyr | Pro | Met | Gly | |
| | | | 725 | | | | | 730 | | | | | 735 | | | |
| GGT | ATA | GAA | GGG | TAT | TGT | CAG | AAG | CTG | TGG | ACC | ATC | AGC | ACC | ATT | CCC | 11492 |
| Gly | Ile | Glu | Gly | Tyr | Cys | Gln | Lys | Leu | Trp | Thr | Ile | Ser | Thr | Ile | Pro | |
| | | | 740 | | | | | 745 | | | | | 750 | | | |
| TAT | CTA | TAC | CTG | GCT | GCT | TAT | GAG | AGC | GGA | GTA | AGG | ATT | GCT | TCG | TTA | 11540 |
| Tyr | Leu | Tyr | Leu | Ala | Ala | Tyr | Glu | Ser | Gly | Val | Arg | Ile | Ala | Ser | Leu | |
| | | 755 | | | | | 760 | | | | | 765 | | | | |
| GTG | CAA | GGG | GAC | AAT | CAG | ACC | ATA | GCC | GTA | ACA | AAA | AGG | GTA | CCC | AGC | 11588 |
| Val | Gln | Gly | Asp | Asn | Gln | Thr | Ile | Ala | Val | Thr | Lys | Arg | Val | Pro | Ser | |
| 770 | | | | | 775 | | | | | 780 | | | | | 785 | |

| | | | | | | | | | | | | | | | | |
|---|---|---|---|---|---|---|---|---|---|---|---|---|---|---|---|---|
| ACA | TGG | CCC | TAC | AAC | CTT | AAG | AAA | CGG | GAA | GCT | GCT | AGA | GTA | ACT | AGA | 11636 |
| Thr | Trp | Pro | Tyr | Asn<br>790 | Leu | Lys | Lys | Arg | Glu<br>795 | Ala | Ala | Arg | Val | Thr<br>800 | Arg | |
| GAT | TAC | TTT | GTA | ATT | CTT | AGG | CAA | AGG | CTA | CAT | GAT | ATT | GGC | CAT | CAC | 11684 |
| Asp | Tyr | Phe | Val<br>805 | Ile | Leu | Arg | Gln | Arg<br>810 | Leu | His | Asp | Ile | Gly<br>815 | His | His | |
| CTC | AAG | GCA | AAT | GAG | ACA | ATT | GTT | TCA | TCA | CAT | TTT | TTT | GTC | TAT | TCA | 11732 |
| Leu | Lys | Ala<br>820 | Asn | Glu | Thr | Ile | Val<br>825 | Ser | Ser | His | Phe | Phe<br>830 | Val | Tyr | Ser | |
| AAA | GGA | ATA | TAT | TAT | GAT | GGG | CTA | CTT | GTG | TCC | CAA | TCA | CTC | AAG | AGC | 11780 |
| Lys | Gly | Ile<br>835 | Tyr | Tyr | Asp | Gly<br>840 | Leu | Leu | Val | Ser | Gln<br>845 | Ser | Leu | Lys | Ser | |
| ATC | GCA | AGA | TGT | GTA | TTC | TGG | TCA | GAG | ACT | ATA | GTT | GAT | GAA | ACA | AGG | 11828 |
| Ile | Ala | Arg | Cys | Val | Phe<br>855 | Trp | Ser | Glu | Thr | Ile<br>860 | Val | Asp | Glu | Thr | Arg<br>865 | |
| 850 | | | | | | | | | | | | | | | | |
| GCA | GCA | TGC | AGT | AAT | ATT | GCT | ACA | ACA | ATG | GCT | AAA | AGC | ATC | GAG | AGA | 11876 |
| Ala | Ala | Cys | Ser | Asn<br>870 | Ile | Ala | Thr | Thr | Met<br>875 | Ala | Lys | Ser | Ile | Glu<br>880 | Arg | |
| GGT | TAT | GAC | CGT | TAC | CTT | GCA | TAT | TCC | CTG | AAC | GTC | CTA | AAA | GTG | ATA | 11924 |
| Gly | Tyr | Asp | Arg<br>885 | Tyr | Leu | Ala | Tyr | Ser<br>890 | Leu | Asn | Val | Leu | Lys<br>895 | Val | Ile | |
| CAG | CAA | ATT | CTG | ATC | TCT | CTT | GGC | TTC | ACA | ATC | AAT | TCA | ACC | ATG | ACC | 11972 |
| Gln | Gln | Ile<br>900 | Leu | Ile | Ser | Leu | Gly<br>905 | Phe | Thr | Ile | Asn | Ser<br>910 | Thr | Met | Thr | |
| CGG | GAT | GTA | GTC | ATA | CCC | CTC | CTC | ACA | AAC | AAC | GAC | CTC | TTA | ATA | AGG | 12020 |
| Arg | Asp<br>915 | Val | Val | Ile | Pro | Leu<br>920 | Leu | Thr | Asn | Asn | Asp<br>925 | Leu | Leu | Ile | Arg | |
| ATG | GCA | CTG | TTG | CCC | GCT | CCT | ATT | GGG | GGG | ATG | AAT | TAT | CTG | AAT | ATG | 12068 |
| Met | Ala | Leu | Leu | Pro<br>935 | Ala | Pro | Ile | Gly | Gly<br>940 | Met | Asn | Tyr | Leu | Asn<br>945 | Met | |
| 930 | | | | | | | | | | | | | | | | |
| AGC | AGG | CTG | TTT | GTC | AGA | AAC | ATC | GGT | GAT | CCA | GTA | ACA | TCA | TCA | ATT | 12116 |
| Ser | Arg | Leu | Phe | Val<br>950 | Arg | Asn | Ile | Gly | Asp<br>955 | Pro | Val | Thr | Ser | Ser<br>960 | Ile | |
| GCT | GAT | CTC | AAG | AGA | ATG | ATT | CTC | GCC | TCA | CTA | ATG | CCT | GAA | GAG | ACC | 12164 |
| Ala | Asp | Leu | Lys<br>965 | Arg | Met | Ile | Leu | Ala<br>970 | Ser | Leu | Met | Pro | Glu<br>975 | Glu | Thr | |
| CTC | CAT | CAA | GTA | ATG | ACA | CAA | CAA | CCG | GGG | GAC | TCT | TCA | TTC | CTA | GAC | 12212 |
| Leu | His | Gln | Val<br>980 | Met | Thr | Gln | Gln | Pro<br>985 | Gly | Asp | Ser | Ser | Phe<br>990 | Leu | Asp | |
| TGG | GCT | AGC | GAC | CCT | TAC | TCA | GCA | AAT | CTT | GTA | TGT | GTC | CAG | AGC | ATC | 12260 |
| Trp | Ala | Ser<br>995 | Asp | Pro | Tyr | Ser | Ala<br>1000 | Asn | Leu | Val | Cys | Val<br>1005 | Gln | Ser | Ile | |
| ACT | AGA | CTC | CTC | AAG | AAC | ATA | ACT | GCA | AGG | TTT | GTC | CTG | ATC | CAT | AGT | 12308 |
| Thr | Arg<br>1010 | Leu | Leu | Lys | Asn<br>1015 | Ile | Thr | Ala | Arg | Phe<br>1020 | Val | Leu | Ile | His | Ser<br>1025 | |
| CCA | AAC | CCA | ATG | TTA | AAA | GGA | TTA | TTC | CAT | GAT | GAC | AGT | AAA | GAA | GAG | 12356 |
| Pro | Asn | Pro | Met | Leu<br>1030 | Lys | Gly | Leu | Phe | His<br>1035 | Asp | Asp | Ser | Lys | Glu<br>1040 | Glu | |
| GAC | GAG | GGA | CTG | GCG | GCA | TTC | CTC | ATG | GAC | AGG | CAT | ATT | ATA | GTA | CCT | 12404 |
| Asp | Glu | Gly | Leu<br>1045 | Ala | Ala | Phe | Leu | Met<br>1050 | Asp | Arg | His | Ile | Ile<br>1055 | Val | Pro | |
| AGG | GCA | GCT | CAT | GAA | ATC | CTG | GAT | CAT | AGT | GTC | ACA | GGG | GCA | AGA | GAG | 12452 |
| Arg | Ala | Ala | His | Glu<br>1060 | Ile | Leu | Asp | His<br>1065 | Ser | Val | Thr | Gly | Ala<br>1070 | Arg | Glu | |
| TCT | ATT | GCA | GGC | ATG | CTG | GAT | ACC | ACA | AAA | GGC | CTG | ATT | CGA | GCC | AGC | 12500 |
| Ser | Ile | Ala<br>1075 | Gly | Met | Leu | Asp | Thr<br>1080 | Thr | Lys | Gly | Leu | Ile<br>1085 | Arg | Ala | Ser | |
| ATG | AGG | AAG | GGG | GGG | TTA | ACC | TCT | CGA | GTG | ATA | ACC | AGA | TTG | TCC | AAT | 12548 |
| Met | Arg | Lys | Gly<br>1090 | Gly | Leu | Thr | Ser<br>1095 | Arg | Val | Ile | Thr<br>1100 | Arg | Leu | Ser | Asn<br>1105 | |

```
TAT GAC TAT GAA CAA TTC AGA GCA GGG ATG GTG CTA TTG ACG GGA AGA       12596
Tyr Asp Tyr Glu Gln Phe Arg Ala Gly Met Val Leu Leu Thr Gly Arg
            1110                    1115                    1120

AAG AGA AAT GTC CTC ATT GAC AAA GAG TCA TGT TCA GTG CAG CTG GCG       12644
Lys Arg Asn Val Leu Ile Asp Lys Glu Ser Cys Ser Val Gln Leu Ala
            1125                    1130                    1135

AGA GCT CTA AGA AGC CAT ATG TGG GCG AGG CTA GCT CGA GGA CGG CCT       12692
Arg Ala Leu Arg Ser His Met Trp Ala Arg Leu Ala Arg Gly Arg Pro
            1140                    1145                    1150

ATT TAC GGC CTT GAG GTC CCT GAT GTA CTA GAA TCT ATG CGA GGC CAC       12740
Ile Tyr Gly Leu Glu Val Pro Asp Val Leu Glu Ser Met Arg Gly His
            1155                    1160                    1165

CTT ATT CGG CGT CAT GAG ACA TGT GTC ATC TGC GAG TGT GGA TCA GTC       12788
Leu Ile Arg Arg His Glu Thr Cys Val Ile Cys Glu Cys Gly Ser Val
1170                    1175                    1180                    1185

AAC TAC GGA TGG TTT TTT GTC CCC TCG GGT TGC CAA CTG GAT GAT ATT       12836
Asn Tyr Gly Trp Phe Phe Val Pro Ser Gly Cys Gln Leu Asp Asp Ile
            1190                    1195                    1200

GAC AAG GAA ACA TCA TCC TTG AGA GTC CCA TAT ATT GGT TCT ACC ACT       12884
Asp Lys Glu Thr Ser Ser Leu Arg Val Pro Tyr Ile Gly Ser Thr Thr
            1205                    1210                    1215

GAT GAG AGA ACA GAC ATG AAG CTT GCC TTC GTA AGA GCC CCA AGT CGA       12932
Asp Glu Arg Thr Asp Met Lys Leu Ala Phe Val Arg Ala Pro Ser Arg
            1220                    1225                    1230

TCC TTG CGA TCT GCT GTT AGA ATA GCA ACA GTG TAC TCA TGG GCT TAC       12980
Ser Leu Arg Ser Ala Val Arg Ile Ala Thr Val Tyr Ser Trp Ala Tyr
            1235                    1240                    1245

GGT GAT GAT GAT AGC TCT TGG AAC GAA GCC TGG TTG TTG GCT AGG CAA       13028
Gly Asp Asp Asp Ser Ser Trp Asn Glu Ala Trp Leu Leu Ala Arg Gln
1250                    1255                    1260                    1265

AGG GCC AAT GTG AGC CTG GAG GAG CTA AGG GTG ATC ACT CCC ATC TCA       13076
Arg Ala Asn Val Ser Leu Glu Glu Leu Arg Val Ile Thr Pro Ile Ser
            1270                    1275                    1280

ACT TCG ACT AAT TTA GCG CAT AGG TTG AGG GAT CGT AGC ACT CAA GTG       13124
Thr Ser Thr Asn Leu Ala His Arg Leu Arg Asp Arg Ser Thr Gln Val
            1285                    1290                    1295

AAA TAC TCA GGT ACA TCC CTT GTC CGA GTG GCG AGG TAT ACC ACA ATC       13172
Lys Tyr Ser Gly Thr Ser Leu Val Arg Val Ala Arg Tyr Thr Thr Ile
            1300                    1305                    1310

TCC AAC GAC AAT CTC TCA TTT GTC ATA TCA GAT AAG AAG GTT GAT ACT       13220
Ser Asn Asp Asn Leu Ser Phe Val Ile Ser Asp Lys Lys Val Asp Thr
            1315                    1320                    1325

AAC TTT ATA TAC CAA CAA GGA ATG CTT CTA GGG TTG GGT GTT TTA GAA       13268
Asn Phe Ile Tyr Gln Gln Gly Met Leu Leu Gly Leu Gly Val Leu Glu
1330                    1335                    1340                    1345

ACA TTG TTT CGA CTC GAG AAA GAT ACC GGA TCA TCT AAC ACG GTA TTA       13316
Thr Leu Phe Arg Leu Glu Lys Asp Thr Gly Ser Ser Asn Thr Val Leu
            1350                    1355                    1360

CAT CTT CAC GTC GAA ACA GAT TGT TGC GTG ATC CCG ATG ATA GAT CAT       13364
His Leu His Val Glu Thr Asp Cys Cys Val Ile Pro Met Ile Asp His
            1365                    1370                    1375

CCC AGG ATA CCC AGC TCC CGC AAG CTA GAG CTG AGG GCA GAG CTA TGT       13412
Pro Arg Ile Pro Ser Ser Arg Lys Leu Glu Leu Arg Ala Glu Leu Cys
            1380                    1385                    1390

ACC AAC CCA TTG ATA TAT GAT AAT GCA CCT TTA ATT GAC AGA GAT ACA       13460
Thr Asn Pro Leu Ile Tyr Asp Asn Ala Pro Leu Ile Asp Arg Asp Thr
            1395                    1400                    1405

ACA AGG CTA TAC ACC CAG AGC CAT AGG AGG CAC CTT GTG GAA TTT GTT       13508
Thr Arg Leu Tyr Thr Gln Ser His Arg Arg His Leu Val Glu Phe Val
1410                    1415                    1420                    1425
```

| | |
|---|---|
| ACA TGG TCC ACA CCC CAA CTA TAT CAC ATT TTA GCT AAG TCC ACA GCA<br>Thr Trp Ser Thr Pro Gln Leu Tyr His Ile Leu Ala Lys Ser Thr Ala<br>　　　　　　1430　　　　　　　　　1435　　　　　　　　1440 | 13556 |
| CTA TCT ATG ATT GAC CTG GTA ACA AAA TTT GAG AAG GAC CAT ATG AAT<br>Leu Ser Met Ile Asp Leu Val Thr Lys Phe Glu Lys Asp His Met Asn<br>　　　　　　1445　　　　　　　　　1450　　　　　　　　1455 | 13604 |
| GAA ATT TCA GCT CTC ATA GGG GAT GAC GAT ATC AAT AGT TTC ATA ACT<br>Glu Ile Ser Ala Leu Ile Gly Asp Asp Asp Ile Asn Ser Phe Ile Thr<br>　　　　　1460　　　　　　　　　1465　　　　　　　　1470 | 13652 |
| GAG TTT CTC GTC ATA GAG CCA AGA TTA TTC ACT ATC TAC TTG GGC CAG<br>Glu Phe Leu Val Ile Glu Pro Arg Leu Phe Thr Ile Tyr Leu Gly Gln<br>　　　1475　　　　　　　　　1480　　　　　　　　1485 | 13700 |
| TGT GCG GCC ATC AAT TGG GCA TTT GAT GTA CAT TAT CAT AGA CCA TCA<br>Cys Ala Ala Ile Asn Trp Ala Phe Asp Val His Tyr His Arg Pro Ser<br>1490　　　　　　　　　1495　　　　　　　　1500　　　　　　　　1505 | 13748 |
| GGG AAA TAT CAG ATG GGT GAG CTG TTG TCA TCG TTC CTT TCT AGA ATG<br>Gly Lys Tyr Gln Met Gly Glu Leu Leu Ser Ser Phe Leu Ser Arg Met<br>　　　　　　1510　　　　　　　　　1515　　　　　　　　1520 | 13796 |
| AGC AAA GGA GTG TTT AAG GTG CTT GTC AAT GCT CTA AGC CAC CCA AAG<br>Ser Lys Gly Val Phe Lys Val Leu Val Asn Ala Leu Ser His Pro Lys<br>　　　　　1525　　　　　　　　　1530　　　　　　　　1535 | 13844 |
| ATC TAC AAG AAA TTC TGG CAT TGT GGT ATT ATA GAG CCT ATC CAT GGT<br>Ile Tyr Lys Lys Phe Trp His Cys Gly Ile Ile Glu Pro Ile His Gly<br>　　　1540　　　　　　　　　1545　　　　　　　　1550 | 13892 |
| CCT TCA CTT GAT GCT CAA AAC TTG CAC ACA ACT GTC TGC AAC ATG GTT<br>Pro Ser Leu Asp Ala Gln Asn Leu His Thr Thr Val Cys Asn Met Val<br>1555　　　　　　　　　1560　　　　　　　　1565 | 13940 |
| TAC ACA TGC TAT ATG ACC TAC CTC GAC CTG TTG TTG AAT GAA GAG TTA<br>Tyr Thr Cys Tyr Met Thr Tyr Leu Asp Leu Leu Leu Asn Glu Glu Leu<br>1570　　　　　　　　　1575　　　　　　　　1580　　　　　　　　1585 | 13988 |
| GAA GAG TTC ACA TTT CTC TTG TGT GAA AGC GAC GAG GAT GTA GTA CCG<br>Glu Glu Phe Thr Phe Leu Leu Cys Glu Ser Asp Glu Asp Val Val Pro<br>　　　　　　1590　　　　　　　　　1595　　　　　　　　1600 | 14036 |
| GAC AGA TTC GAC AAC ATC CAG GCA AAA CAC TTA TGT GTT CTG GCA GAT<br>Asp Arg Phe Asp Asn Ile Gln Ala Lys His Leu Cys Val Leu Ala Asp<br>　　　　　1605　　　　　　　　　1610　　　　　　　　1615 | 14084 |
| TTG TAC TGT CAA CCA GGG GCC TGC CCA CCA ATT CGA GGT CTA AGA CCG<br>Leu Tyr Cys Gln Pro Gly Ala Cys Pro Pro Ile Arg Gly Leu Arg Pro<br>　　　1620　　　　　　　　　1625　　　　　　　　1630 | 14132 |
| GTA GAG AAA TGT GCA GTT CTA ACC GAC CAT ATC AAG GCA GAG GCT AGG<br>Val Glu Lys Cys Ala Val Leu Thr Asp His Ile Lys Ala Glu Ala Arg<br>1635　　　　　　　　　1640　　　　　　　　1645 | 14180 |
| TTA TCT CCA GCA GGA TCT TCG TGG AAC ATA AAT CCA ATT ATT GTA GAC<br>Leu Ser Pro Ala Gly Ser Ser Trp Asn Ile Asn Pro Ile Ile Val Asp<br>1650　　　　　　　　　1655　　　　　　　　1660　　　　　　　　1665 | 14228 |
| CAT TAC TCA TGC TCT CTG ACT TAT CTC CGG CGA GGA TCG ATC AAA CAG<br>His Tyr Ser Cys Ser Leu Thr Tyr Leu Arg Arg Gly Ser Ile Lys Gln<br>　　　　　　1670　　　　　　　　　1675　　　　　　　　1680 | 14276 |
| ATA AGA TTG AGA GTT GAT CCA GGA TTC ATT TTC GAC GCC CTC GCT GAG<br>Ile Arg Leu Arg Val Asp Pro Gly Phe Ile Phe Asp Ala Leu Ala Glu<br>　　　　　1685　　　　　　　　　1690　　　　　　　　1695 | 14324 |
| GTA AAT GTC AGT CAG CCA AAG ATC GGC AGC AAC AAC ATC TCA AAT ATG<br>Val Asn Val Ser Gln Pro Lys Ile Gly Ser Asn Asn Ile Ser Asn Met<br>　　　1700　　　　　　　　　1705　　　　　　　　1710 | 14372 |
| AGC ATC AAG GCT TTC AGA CCC CCA CAC GAT GAT GTT GCA AAA TTG CTC<br>Ser Ile Lys Ala Phe Arg Pro Pro His Asp Asp Val Ala Lys Leu Leu<br>1715　　　　　　　　　1720　　　　　　　　1725 | 14420 |
| AAA GAT ATC AAC ACA AGC AAG CAC AAT CTT CCC ATT TCA GGG GGC AAT<br>Lys Asp Ile Asn Thr Ser Lys His Asn Leu Pro Ile Ser Gly Gly Asn<br>1730　　　　　　　　　1735　　　　　　　　1740　　　　　　　　1745 | 14468 |

| | |
|---|---|
| CTC GCC AAT TAT GAA ATC CAT GCT TTC CGC AGA ATC GGG TTG AAC TCA<br>Leu Ala Asn Tyr Glu Ile His Ala Phe Arg Arg Ile Gly Leu Asn Ser<br>1750 1755 1760 | 14516 |
| TCT GCT TGC TAC AAA GCT GTT GAG ATA TCA ACA TTA ATT AGG AGA TGC<br>Ser Ala Cys Tyr Lys Ala Val Glu Ile Ser Thr Leu Ile Arg Arg Cys<br>1765 1770 1775 | 14564 |
| CTT GAG CCA GGG GAG GAC GGC TTG TTC TTG GGT GAG GGA TCG GGT TCT<br>Leu Glu Pro Gly Glu Asp Gly Leu Phe Leu Gly Glu Gly Ser Gly Ser<br>1780 1785 1790 | 14612 |
| ATG TTG ATC ACT TAT AAG GAG ATA CTT AAA CTA AAC AAG TGC TTC TAT<br>Met Leu Ile Thr Tyr Lys Glu Ile Leu Lys Leu Asn Lys Cys Phe Tyr<br>1795 1800 1805 | 14660 |
| AAT AGT GGG GTT TCC GCC AAT TCT AGA TCT GGT CAA AGG GAA TTA GCA<br>Asn Ser Gly Val Ser Ala Asn Ser Arg Ser Gly Gln Arg Glu Leu Ala<br>1810 1815 1820 1825 | 14708 |
| CCC TAT CCC TCC GAA GTT GGC CTT GTC GAA CAC AGA ATG GGA GTA GGT<br>Pro Tyr Pro Ser Glu Val Gly Leu Val Glu His Arg Met Gly Val Gly<br>1830 1835 1840 | 14756 |
| AAT ATT GTC AAA GTG CTC TTT AAC GGG AGG CCC GAA GTC ACG TGG GTA<br>Asn Ile Val Lys Val Leu Phe Asn Gly Arg Pro Glu Val Thr Trp Val<br>1845 1850 1855 | 14804 |
| GGC AGT GTA GAT TGC TTC AAT TTC ATA GTT AGT AAT ATC CCT ACC TCT<br>Gly Ser Val Asp Cys Phe Asn Phe Ile Val Ser Asn Ile Pro Thr Ser<br>1860 1865 1870 | 14852 |
| AGT GTG GGG TTT ATC CAT TCA GAT ATA GAG ACC TTG CCT AAC AAA GAT<br>Ser Val Gly Phe Ile His Ser Asp Ile Glu Thr Leu Pro Asn Lys Asp<br>1875 1880 1885 | 14900 |
| ACT ATA GAG AAG CTA GAG GAA TTG GCA GCC ATC TTA TCG ATG GCT CTG<br>Thr Ile Glu Lys Leu Glu Glu Leu Ala Ala Ile Leu Ser Met Ala Leu<br>1890 1895 1900 1905 | 14948 |
| CTC CTG GGC AAA ATA GGA TCA ATA CTG GTG ATT AAG CTT ATG CCT TTC<br>Leu Leu Gly Lys Ile Gly Ser Ile Leu Val Ile Lys Leu Met Pro Phe<br>1910 1915 1920 | 14996 |
| AGC GGG GAT TTT GTT CAG GGA TTT ATA AGT TAT GTA GGG TCT TAT TAT<br>Ser Gly Asp Phe Val Gln Gly Phe Ile Ser Tyr Val Gly Ser Tyr Tyr<br>1925 1930 1935 | 15044 |
| AGA GAA GTG AAC CTT GTA TAC CCT AGA TAC AGC AAC TTC ATA TCT ACT<br>Arg Glu Val Asn Leu Val Tyr Pro Arg Tyr Ser Asn Phe Ile Ser Thr<br>1940 1945 1950 | 15092 |
| GAA TCT TAT TTG GTT ATG ACA GAT CTC AAG GCT AAC CGG CTA ATG AAT<br>Glu Ser Tyr Leu Val Met Thr Asp Leu Lys Ala Asn Arg Leu Met Asn<br>1955 1960 1965 | 15140 |
| CCT GAA AAG ATT AAG CAG CAG ATA ATT GAA TCA TCT GTG AGG ACT TCA<br>Pro Glu Lys Ile Lys Gln Gln Ile Ile Glu Ser Ser Val Arg Thr Ser<br>1970 1975 1980 1985 | 15188 |
| CCT GGA CTT ATA GGT CAC ATC CTA TCC ATT AAG CAA CTA AGC TGC ATA<br>Pro Gly Leu Ile Gly His Ile Leu Ser Ile Lys Gln Leu Ser Cys Ile<br>1990 1995 2000 | 15236 |
| CAA GCA ATT GTG GGA GAC GTA GTT AGT AGA GGT GAT ATC AAT CCT ACT<br>Gln Ala Ile Val Gly Asp Val Val Ser Arg Gly Asp Ile Asn Pro Thr<br>2005 2010 2015 | 15284 |
| CTG AAA AAA CTT ACA CCT ATA GAG CAG GTG CTG ATC AAT TGC GGG TTG<br>Leu Lys Lys Leu Thr Pro Ile Glu Gln Val Leu Ile Asn Cys Gly Leu<br>2020 2025 2030 | 15332 |
| GCA ATT AAC GGA CCT AAG CTG TGC AAA GAA TTG ATC CAC CAT GAT GTT<br>Ala Ile Asn Gly Pro Lys Leu Cys Lys Glu Leu Ile His His Asp Val<br>2035 2040 2045 | 15380 |
| GCC TCA GGG CAA GAT GGA TTG CTT AAT TCT ATC CTC ATC CTC TAC AGG<br>Ala Ser Gly Gln Asp Gly Leu Leu Asn Ser Ile Leu Ile Leu Tyr Arg<br>2050 2055 2060 2065 | 15428 |

```
GAG TTG GCA AGA TTC AAA GAC AAC CGA AGA AGT CAA CAA GGG ATG TTC      15476
Glu Leu Ala Arg Phe Lys Asp Asn Arg Arg Ser Gln Gln Gly Met Phe
            2070                2075                2080

CAC GCT TAC CCC GTA TTG GTA AGT AGC AGG CAA CGA GAA CTT ATA TCT      15524
His Ala Tyr Pro Val Leu Val Ser Ser Arg Gln Arg Glu Leu Ile Ser
            2085                2090                2095

AGG ATC ACC CGC AAA TTT TGG GGG CAC ATT CTT CTT TAC TCC GGG AAC      15572
Arg Ile Thr Arg Lys Phe Trp Gly His Ile Leu Leu Tyr Ser Gly Asn
            2100                2105                2110

AGA AAG TTG ATA AAT AAG TTT ATC CAG AAT CTC AAG TCC GGC TAT CTG      15620
Arg Lys Leu Ile Asn Lys Phe Ile Gln Asn Leu Lys Ser Gly Tyr Leu
            2115                2120                2125

ATA CTA GAC TTA CAC CAG AAT ATC TTC GTT AAG AAT CTA TCC AAG TCA      15668
Ile Leu Asp Leu His Gln Asn Ile Phe Val Lys Asn Leu Ser Lys Ser
2130            2135                2140                2145

GAG AAA CAG ATT ATT ATG ACG GGG GGT TTG AAA CGT GAG TGG GTT TTT      15716
Glu Lys Gln Ile Ile Met Thr Gly Gly Leu Lys Arg Glu Trp Val Phe
            2150                2155                2160

AAG GTA ACA GTC AAG GAG ACC AAA GAA TGG TAT AAG TTA GTC GGA TAC      15764
Lys Val Thr Val Lys Glu Thr Lys Glu Trp Tyr Lys Leu Val Gly Tyr
            2165                2170                2175

AGT GCC CTG ATT AAG GAC TAATTGGTTG AACTCCGGAA CCCTAATCCT             15812
Ser Ala Leu Ile Lys Asp
            2180

GCCCTAGGTG GTTAGGCATT ATTTGCAATA TATTAAAGAA AACTTTGAAA ATACGAAGTT    15872

TCTATTCCCA GCTTTGTCTG GT                                             15894
```

( 2 ) INFORMATION FOR SEQ ID NO:2:

( i ) SEQUENCE CHARACTERISTICS:
        ( A ) LENGTH: 525 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Thr Leu Leu Arg Ser Leu Ala Leu Phe Lys Arg Asn Lys Asp
 1               5                  10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Lys Tyr Phe Ser His Asp Pro Ile Ser Ser Asp Gln Ser Arg Phe
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175
```

| | | | | | | | | | | | | | | |
|---|---|---|---|---|---|---|---|---|---|---|---|---|---|---|
| Leu | Leu | Ala | Lys 180 | Ala | Val | Thr | Ala | Pro 185 | Asp | Thr | Ala | Ala | Asp 190 | Ser | Glu |
| Leu | Arg | Arg 195 | Trp | Ile | Lys | Tyr | Thr 200 | Gln | Gln | Arg | Arg | Val 205 | Val | Gly | Glu |
| Phe | Arg 210 | Leu | Glu | Arg | Lys | Trp 215 | Leu | Asp | Val | Val | Arg 220 | Asn | Arg | Ile | Ala |
| Glu 225 | Asp | Leu | Ser | Leu | Arg 230 | Arg | Phe | Met | Val | Ala 235 | Leu | Ile | Leu | Asp | Ile 240 |
| Lys | Arg | Thr | Pro | Asn 245 | Lys | Pro | Arg | Ile 250 | Ala | Glu | Met | Ile | Cys 255 | Asp |
| Ile | Asp | Thr | Tyr 260 | Ile | Val | Glu | Ala | Gly 265 | Leu | Ala | Ser | Phe | Ile 270 | Leu | Thr |
| Ile | Lys | Phe 275 | Gly | Ile | Glu | Thr | Met 280 | Tyr | Pro | Ala | Leu | Gly 285 | Leu | His | Glu |
| Phe | Ala 290 | Gly | Glu | Leu | Ser | Thr 295 | Leu | Glu | Ser | Leu | Met 300 | Asn | Leu | Tyr | Gln |
| Gln 305 | Met | Gly | Glu | Thr | Ala 310 | Pro | Tyr | Met | Val | Asn 315 | Leu | Glu | Asn | Ser | Ile 320 |
| Gln | Asn | Lys | Phe | Ser 325 | Ala | Gly | Ser | Tyr | Pro 330 | Leu | Leu | Trp | Ser | Tyr 335 | Ala |
| Met | Gly | Val | Gly 340 | Val | Glu | Leu | Glu | Asn 345 | Ser | Met | Gly | Gly | Leu 350 | Asn | Phe |
| Gly | Arg | Ser 355 | Tyr | Phe | Asp | Pro | Ala 360 | Tyr | Phe | Arg | Leu | Gly 365 | Gln | Glu | Met |
| Val | Arg 370 | Arg | Ser | Ala | Gly | Lys 375 | Val | Ser | Ser | Thr | Leu 380 | Ala | Ser | Glu | Leu |
| Gly 385 | Ile | Thr | Ala | Glu | Asp 390 | Ala | Arg | Leu | Val | Ser 395 | Glu | Ile | Ala | Met | His 400 |
| Thr | Thr | Glu | Asp | Lys 405 | Ile | Ser | Arg | Ala | Val 410 | Gly | Pro | Arg | Gln | Ala 415 | Gln |
| Val | Ser | Phe | Leu 420 | His | Gly | Asp | Gln | Ser 425 | Glu | Asn | Glu | Leu | Pro 430 | Arg | Leu |
| Gly | Gly | Lys 435 | Glu | Asp | Arg | Arg | Val 440 | Lys | Gln | Ser | Arg | Gly 445 | Glu | Ala | Arg |
| Glu | Ser 450 | Tyr | Arg | Glu | Thr | Gly 455 | Pro | Ser | Arg | Ala | Ser 460 | Asp | Ala | Arg | Ala |
| Ala 465 | His | Leu | Pro | Thr | Gly 470 | Thr | Pro | Leu | Asp | Ile 475 | Asp | Thr | Ala | Ser | Glu 480 |
| Ser | Ser | Gln | Asp | Pro 485 | Gln | Asp | Ser | Arg | Arg 490 | Ser | Ala | Asp | Ala | Leu 495 | Leu |
| Arg | Leu | Gln | Ala | Met 500 | Ala | Gly | Ile | Ser 505 | Glu | Gln | Gly | Ser 510 | Asp | Thr |
| Asp | Thr | Pro 515 | Ile | Val | Tyr | Asn | Asp 520 | Arg | Asn | Leu | Leu | Asp 525 |

( 2 ) INFORMATION FOR SEQ ID NO:3:

( i ) SEQUENCE CHARACTERISTICS:
    ( A ) LENGTH: 507 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

Met Ala Glu Glu Gln Ala Arg His Val Lys Asn Gly Leu Glu Cys Ile

|  1 |  |  |  |  5 |  |  |  |  10 |  |  |  |  15 |  |  |
|---|---|---|---|---|---|---|---|---|---|---|---|---|---|---|
| Arg | Ala | Leu | Lys | Ala | Glu | Pro | Ile | Gly | Ser | Leu | Ala | Ile | Glu | Ala |
|  |  |  | 20 |  |  |  |  | 25 |  |  |  | 30 |  |  |
| Met | Ala | Ala | Trp | Ser | Glu | Ile | Ser | Asp | Asn | Pro | Gly | Gln | Glu | Arg | Ala |
|  |  | 35 |  |  |  |  | 40 |  |  |  |  | 45 |  |  |
| Thr | Cys | Arg | Glu | Glu | Lys | Ala | Gly | Ser | Ser | Gly | Leu | Ser | Lys | Pro | Cys |
|  | 50 |  |  |  |  | 55 |  |  |  |  | 60 |  |  |  |
| Leu | Ser | Ala | Ile | Gly | Ser | Thr | Glu | Gly | Gly | Ala | Pro | Arg | Ile | Arg | Gly |
| 65 |  |  |  |  | 70 |  |  |  |  | 75 |  |  |  |  | 80 |
| Gln | Gly | Pro | Gly | Glu | Ser | Asp | Asp | Ala | Glu | Thr | Leu | Gly | Ile | Pro |
|  |  |  |  | 85 |  |  |  |  | 90 |  |  |  |  | 95 |
| Pro | Arg | Asn | Leu | Gln | Ala | Ser | Ser | Thr | Gly | Leu | Gln | Cys | Tyr | Tyr | Val |
|  |  |  | 100 |  |  |  |  | 105 |  |  |  |  | 110 |  |  |
| Tyr | Asp | His | Ser | Gly | Glu | Ala | Val | Lys | Gly | Ile | Gln | Asp | Ala | Asp | Ser |
|  |  | 115 |  |  |  |  | 120 |  |  |  |  | 125 |  |  |  |
| Ile | Met | Val | Gln | Ser | Gly | Leu | Asp | Gly | Asp | Ser | Thr | Leu | Ser | Gly | Gly |
|  | 130 |  |  |  |  | 135 |  |  |  |  | 140 |  |  |  |  |
| Asp | Asn | Glu | Ser | Glu | Asn | Ser | Asp | Val | Asp | Ile | Gly | Glu | Pro | Asp | Thr |
| 145 |  |  |  |  | 150 |  |  |  |  | 155 |  |  |  |  | 160 |
| Glu | Gly | Tyr | Ala | Ile | Thr | Asp | Arg | Gly | Ser | Ala | Pro | Ile | Ser | Met | Gly |
|  |  |  |  | 165 |  |  |  |  | 170 |  |  |  |  | 175 |  |
| Phe | Arg | Ala | Ser | Asp | Val | Glu | Thr | Ala | Glu | Gly | Gly | Glu | Ile | His | Glu |
|  |  |  | 180 |  |  |  |  | 185 |  |  |  |  | 190 |  |  |
| Leu | Leu | Arg | Leu | Gln | Ser | Arg | Gly | Asn | Asn | Phe | Pro | Lys | Leu | Gly | Lys |
|  |  | 195 |  |  |  |  | 200 |  |  |  |  | 205 |  |  |  |
| Thr | Leu | Asn | Val | Pro | Pro | Pro | Asp | Pro | Gly | Arg | Ala | Ser | Thr | Ser |
|  | 210 |  |  |  |  | 215 |  |  |  |  | 220 |  |  |  |
| Gly | Thr | Pro | Ile | Lys | Lys | Gly | Thr | Glu | Arg | Arg | Leu | Ala | Ser | Phe | Gly |
| 225 |  |  |  |  | 230 |  |  |  |  | 235 |  |  |  |  | 240 |
| Thr | Glu | Ile | Ala | Ser | Leu | Leu | Thr | Gly | Gly | Ala | Thr | Gln | Cys | Ala | Arg |
|  |  |  |  | 245 |  |  |  |  | 250 |  |  |  |  | 255 |  |
| Lys | Ser | Pro | Ser | Glu | Pro | Ser | Gly | Pro | Gly | Ala | Pro | Ala | Gly | Asn | Val |
|  |  |  | 260 |  |  |  |  | 265 |  |  |  |  | 270 |  |  |
| Pro | Glu | Tyr | Val | Ser | Asn | Ala | Ala | Leu | Ile | Gln | Glu | Trp | Thr | Pro | Glu |
|  |  | 275 |  |  |  |  | 280 |  |  |  |  | 285 |  |  |  |
| Ser | Gly | Thr | Thr | Ile | Ser | Pro | Arg | Ser | Gln | Asn | Asn | Glu | Glu | Gly | Gly |
|  | 290 |  |  |  |  | 295 |  |  |  |  | 300 |  |  |  |  |
| Asp | Tyr | Tyr | Asp | Asp | Glu | Leu | Phe | Ser | Asp | Val | Gln | Asp | Ile | Lys | Thr |
| 305 |  |  |  |  | 310 |  |  |  |  | 315 |  |  |  |  | 320 |
| Ala | Leu | Ala | Lys | Ile | His | Glu | Asp | Asn | Gln | Lys | Ile | Ile | Ser | Lys | Leu |
|  |  |  |  | 325 |  |  |  |  | 330 |  |  |  |  | 335 |  |
| Glu | Ser | Leu | Leu | Leu | Leu | Lys | Gly | Glu | Val | Glu | Ser | Ile | Lys | Lys | Gln |
|  |  |  | 340 |  |  |  |  | 345 |  |  |  |  | 350 |  |  |
| Ile | Asn | Arg | Gln | Asn | Ile | Ser | Ile | Ser | Thr | Leu | Glu | Gly | His | Leu | Ser |
|  |  | 355 |  |  |  |  | 360 |  |  |  |  | 365 |  |  |  |
| Ser | Ile | Met | Ile | Ala | Ile | Pro | Gly | Leu | Gly | Lys | Asp | Pro | Asn | Asp | Pro |
|  | 370 |  |  |  |  | 375 |  |  |  |  | 380 |  |  |  |  |
| Thr | Ala | Asp | Val | Glu | Ile | Asn | Pro | Asp | Leu | Lys | Pro | Ile | Ile | Gly | Arg |
| 385 |  |  |  |  | 390 |  |  |  |  | 395 |  |  |  |  | 400 |
| Asp | Ser | Gly | Arg | Ala | Leu | Ala | Glu | Val | Leu | Lys | Lys | Pro | Val | Ala | Ser |
|  |  |  |  | 405 |  |  |  |  | 410 |  |  |  |  | 415 |  |
| Arg | Gln | Leu | Gln | Gly | Met | Thr | Asn | Gly | Arg | Thr | Ser | Ser | Arg | Gly | Gln |
|  |  |  | 420 |  |  |  |  | 425 |  |  |  |  | 430 |  |  |

| Leu | Leu | Lys<br>435 | Glu | Phe | Gln | Pro | Lys<br>440 | Pro | Ile | Gly | Lys | Lys<br>445 | Met | Ser | Ser |

| Ala | Val | Gly<br>450 | Phe | Val | Pro | Asp | Thr<br>455 | Gly | Pro | Ala | Ser<br>460 | Arg | Ser | Val | Ile |

| Arg<br>465 | Ser | Ile | Ile | Lys | Ser<br>470 | Ser | Arg | Leu | Glu | Glu<br>475 | Asp | Arg | Lys | Arg | Tyr<br>480 |

| Leu | Met | Thr | Leu | Leu<br>485 | Asp | Asp | Ile | Lys | Gly<br>490 | Ala | Asn | Asp | Leu | Ala<br>495 | Lys |

| Phe | His | Gln | Met<br>500 | Leu | Met | Lys | Ile | Ile<br>505 | Met | Lys |

( 2 ) INFORMATION FOR SEQ ID NO:4:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met<br>1 | Thr | Glu | Ile | Tyr<br>5 | Asp | Phe | Asp | Lys | Ser<br>10 | Ala | Trp | Asp | Ile | Lys<br>15 | Gly |

| Ser | Ile | Ala | Pro<br>20 | Ile | Gln | Pro | Thr | Thr<br>25 | Tyr | Ser | Asp | Gly | Arg<br>30 | Leu | Val |

| Pro | Gln | Val<br>35 | Arg | Val | Ile | Asp | Pro<br>40 | Gly | Leu | Gly | Asp | Arg<br>45 | Lys | Asp | Glu |

| Cys | Phe<br>50 | Met | Tyr | Met | Ser | Leu<br>55 | Leu | Gly | Val | Val | Glu<br>60 | Asp | Ser | Asp | Pro |

| Leu<br>65 | Gly | Pro | Pro | Ile | Gly<br>70 | Arg | Ala | Phe | Gly | Ser<br>75 | Leu | Pro | Leu | Gly | Val<br>80 |

| Gly | Arg | Ser | Thr | Ala<br>85 | Lys | Pro | Glu | Lys | Leu<br>90 | Leu | Lys | Glu | Ala | Thr<br>95 | Glu |

| Leu | Asp | Ile | Val<br>100 | Val | Arg | Arg | Thr | Ala<br>105 | Gly | Leu | Asn | Glu | Lys<br>110 | Leu | Val |

| Phe | Tyr | Asn<br>115 | Asn | Thr | Pro | Leu | Thr<br>120 | Leu | Leu | Thr | Pro | Trp<br>125 | Arg | Lys | Val |

| Leu | Thr<br>130 | Thr | Gly | Ser | Val | Phe<br>135 | Asn | Ala | Asn | Gln | Val<br>140 | Cys | Asn | Ala | Val |

| Asn<br>145 | Leu | Ile | Pro | Leu | Asp<br>150 | Thr | Pro | Gln | Arg | Phe<br>155 | Arg | Val | Val | Tyr | Met<br>160 |

| Ser | Ile | Thr | Arg | Leu<br>165 | Ser | Asp | Asn | Gly | Tyr<br>170 | Tyr | Thr | Val | Pro | Arg<br>175 | Arg |

| Met | Leu | Glu | Phe<br>180 | Arg | Ser | Val | Asn | Ala<br>185 | Val | Ala | Phe | Asn | Leu<br>190 | Leu | Val |

| Thr | Leu | Arg<br>195 | Ile | Asp | Lys | Ala | Ile<br>200 | Gly | Pro | Gly | Lys | Ile<br>205 | Ile | Asp | Asn |

| Thr | Glu<br>210 | Gln | Leu | Pro | Glu | Ala<br>215 | Thr | Phe | Met | Val | His<br>220 | Ile | Gly | Asn | Phe |

| Arg<br>225 | Arg | Lys | Lys | Ser | Glu<br>230 | Val | Tyr | Ser | Ala | Asp<br>235 | Tyr | Cys | Lys | Met | Lys<br>240 |

| Ile | Glu | Lys | Met | Gly<br>245 | Leu | Val | Phe | Ala | Leu<br>250 | Gly | Gly | Ile | Gly | Gly<br>255 | Thr |

| Ser | Leu | His | Ile<br>260 | Arg | Ser | Thr | Gly | Lys<br>265 | Met | Ser | Lys | Thr | Leu<br>270 | His | Ala |

| Gln | Leu | Gly<br>275 | Phe | Lys | Lys | Thr | Leu<br>280 | Cys | Tyr | Pro | Leu | Met<br>285 | Asp | Ile | Asn |

```
Glu Asp Leu Asn Arg Leu Leu Trp Arg Ser Arg Cys Lys Ile Val Arg
    290                 295                 300

Ile Gln Ala Val Leu Gln Pro Ser Val Pro Gln Glu Phe Arg Ile Tyr
305                 310                 315                 320

Asp Asp Val Ile Ile Asn Asp Asp Gln Gly Leu Phe Lys Val Leu
                325                 330                 335
```

( 2 ) INFORMATION FOR SEQ ID NO:5:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Gly Leu Lys Val Asn Val Ser Ala Ile Phe Met Ala Val Leu Leu
1                   5                   10                  15

Thr Leu Gln Thr Pro Thr Gly Gln Ile His Trp Gly Asn Leu Ser Lys
                20                  25                  30

Ile Gly Val Val Gly Ile Gly Ser Ala Ser Tyr Lys Val Met Thr Arg
                35                  40                  45

Ser Ser His Gln Ser Leu Val Ile Lys Leu Met Pro Asn Ile Thr Leu
    50                  55                  60

Leu Asn Asn Cys Thr Arg Val Glu Ile Ala Glu Tyr Arg Arg Leu Leu
65                  70                  75                  80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
                100                 105                 110

Phe Ala Gly Val Val Leu Ala Gly Ala Ala Leu Gly Val Ala Thr Ala
                115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
                180                 185                 190

Leu Ser Cys Asp Leu Ile Gly Gln Lys Leu Gly Leu Lys Leu Leu Arg
    195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
                260                 265                 270

Asp Thr Glu Ser Tyr Leu Ile Val Leu Ser Ile Ala Tyr Pro Thr Leu
    275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
```

|     |     |     |     |     |     |     |     |     |     |     |     |     |     |     |     |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |
| Thr | Gln | Gly | Tyr | Leu | Ile | Ser | Asn | Phe | Asp | Glu | Ser | Ser | Cys | Thr | Phe |
|     |     |     |     | 325 |     |     |     |     | 330 |     |     |     |     | 335 |     |
| Met | Pro | Glu | Gly | Thr | Val | Cys | Ser | Gln | Asn | Ala | Leu | Tyr | Pro | Met | Ser |
|     |     |     | 340 |     |     |     |     |     | 345 |     |     |     |     | 350 |     |
| Pro | Leu | Leu | Gln | Glu | Cys | Leu | Arg | Gly | Ser | Thr | Lys | Ser | Cys | Ala | Arg |
|     |     | 355 |     |     |     |     |     | 360 |     |     |     |     | 365 |     |     |
| Thr | Leu | Val | Ser | Gly | Ser | Phe | Gly | Asn | Arg | Phe | Ile | Leu | Ser | Gln | Gly |
|     |     | 370 |     |     |     |     | 375 |     |     |     |     | 380 |     |     |     |
| Asn | Leu | Ile | Ala | Asn | Cys | Ala | Ser | Ile | Leu | Cys | Lys | Cys | Tyr | Thr | Thr |
| 385 |     |     |     |     | 390 |     |     |     |     | 395 |     |     |     |     | 400 |
| Gly | Thr | Ile | Ile | Asn | Gln | Asp | Pro | Asp | Lys | Ile | Leu | Thr | Tyr | Ile | Ala |
|     |     |     |     | 405 |     |     |     |     | 410 |     |     |     |     | 415 |     |
| Ala | Asp | His | Cys | Pro | Val | Val | Glu | Val | Asn | Gly | Val | Thr | Ile | Gln | Val |
|     |     |     | 420 |     |     |     |     |     | 425 |     |     |     |     | 430 |     |
| Gly | Ser | Arg | Arg | Tyr | Pro | Asp | Ala | Val | Tyr | Leu | His | Arg | Ile | Asp | Leu |
|     |     | 435 |     |     |     |     | 440 |     |     |     |     | 445 |     |     |     |
| Gly | Pro | Pro | Ile | Leu | Leu | Glu | Arg | Leu | Asp | Val | Gly | Thr | Asn | Leu | Gly |
|     | 450 |     |     |     |     | 455 |     |     |     |     | 460 |     |     |     |     |
| Asn | Ala | Ile | Ala | Lys | Leu | Glu | Asp | Ala | Lys | Glu | Leu | Leu | Glu | Ser | Ser |
| 465 |     |     |     |     | 470 |     |     |     |     | 475 |     |     |     |     | 480 |
| Asp | Gln | Ile | Leu | Arg | Ser | Met | Lys | Gly | Leu | Ser | Ser | Thr | Cys | Ile | Val |
|     |     |     |     | 485 |     |     |     |     | 490 |     |     |     |     | 495 |     |
| Tyr | Ile | Leu | Ile | Ala | Val | Cys | Leu | Gly | Gly | Leu | Ile | Gly | Ile | Pro | Ala |
|     |     |     | 500 |     |     |     |     |     | 505 |     |     |     |     | 510 |     |
| Leu | Ile | Cys | Cys | Cys | Arg | Gly | Arg | Cys | Asn | Lys | Lys | Gly | Glu | Gln | Val |
|     |     | 515 |     |     |     |     |     | 520 |     |     |     |     | 525 |     |     |
| Gly | Met | Ser | Arg | Pro | Gly | Leu | Lys | Pro | Asp | Leu | Thr | Gly | Thr | Ser | Lys |
|     | 530 |     |     |     |     | 535 |     |     |     |     | 540 |     |     |     |     |
| Ser | Tyr | Val | Arg | Ser | Leu |     |     |     |     |     |     |     |     |     |     |
| 545 |     |     |     |     | 550 |     |     |     |     |     |     |     |     |     |     |

( 2 ) INFORMATION FOR SEQ ID NO:6:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ser | Pro | Gln | Arg | Asp | Arg | Ile | Asn | Ala | Phe | Tyr | Lys | Asp | Asn | Pro |
| 1   |     |     |     | 5   |     |     |     |     | 10  |     |     |     |     | 15  |     |
| His | Pro | Lys | Gly | Ser | Arg | Ile | Val | Ile | Asn | Arg | Glu | His | Leu | Met | Ile |
|     |     |     | 20  |     |     |     |     |     | 25  |     |     |     |     | 30  |     |
| Asp | Arg | Pro | Tyr | Val | Leu | Leu | Ala | Val | Leu | Phe | Val | Met | Phe | Leu | Ser |
|     |     | 35  |     |     |     |     | 40  |     |     |     |     | 45  |     |     |     |
| Leu | Ile | Gly | Leu | Leu | Ala | Ile | Ala | Gly | Ile | Arg | Leu | His | Arg | Ala | Ala |
|     | 50  |     |     |     |     | 55  |     |     |     |     | 60  |     |     |     |     |
| Ile | Tyr | Thr | Ala | Glu | Ile | His | Lys | Ser | Leu | Ser | Thr | Asn | Leu | Asp | Val |
| 65  |     |     |     |     | 70  |     |     |     |     | 75  |     |     |     |     | 80  |
| Thr | Asn | Ser | Ile | Glu | His | Gln | Val | Lys | Asp | Val | Leu | Thr | Pro | Leu | Phe |
|     |     |     |     | 85  |     |     |     |     | 90  |     |     |     |     | 95  |     |
| Lys | Ile | Ile | Gly | Asp | Glu | Val | Gly | Leu | Arg | Thr | Pro | Gln | Arg | Phe | Thr |
|     |     |     | 100 |     |     |     |     |     | 105 |     |     |     |     | 110 |     |

-continued

```
Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Met Asn Pro Pro Glu
        130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Arg Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Thr Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Tyr Leu Phe Asn Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540
```

```
Pro  Ser  Arg  Ser  Phe  Ser  Tyr  Phe  Tyr  Pro  Phe  Arg  Leu  Pro  Ile  Lys
545                      550                      555                      560

Gly  Val  Pro  Ile  Glu  Leu  Gln  Val  Glu  Cys  Phe  Thr  Trp  Asp  Gln  Lys
                         565                      570                      575

Leu  Trp  Cys  Arg  His  Phe  Cys  Val  Leu  Ala  Asp  Ser  Glu  Ser  Gly  Gly
                    580                       585                      590

His  Ile  Thr  His  Ser  Gly  Met  Val  Gly  Met  Gly  Val  Ser  Cys  Thr  Val
               595                 600                      605

Thr  Arg  Glu  Asp  Gly  Thr  Asn  Arg  Arg
610                           615
```

( 2 ) INFORMATION FOR SEQ ID NO:7:

( i ) SEQUENCE CHARACTERISTICS:
       ( A ) LENGTH: 2183 amino acids
       ( B ) TYPE: amino acid
       ( D ) TOPOLOGY: linear ( i i ) MOLECULE TYPE: protein ( x i ) SEQUENCE DESCRIPTION: SEQ ID NO:7:

```
Met  Asp  Ser  Leu  Ser  Val  Asn  Gln  Ile  Leu  Tyr  Pro  Glu  Val  His  Leu
  1            5                      10                      15

Asp  Ser  Pro  Ile  Val  Thr  Asn  Lys  Ile  Val  Ala  Ile  Leu  Glu  Tyr  Ala
               20                      25                      30

Arg  Val  Pro  His  Ala  Tyr  Ser  Leu  Glu  Asp  Pro  Thr  Leu  Cys  Gln  Asn
               35                      40                      45

Ile  Lys  His  Arg  Leu  Lys  Asn  Gly  Phe  Ser  Asn  Gln  Met  Ile  Ile  Asn
     50                      55                      60

Asn  Val  Glu  Val  Gly  Asn  Val  Ile  Lys  Ser  Lys  Leu  Arg  Ser  Tyr  Pro
65                       70                      75                       80

Ala  His  Ser  His  Ile  Pro  Tyr  Pro  Asn  Cys  Asn  Gln  Asp  Leu  Phe  Asn
               85                      90                      95

Ile  Glu  Asp  Lys  Glu  Ser  Thr  Arg  Lys  Ile  Arg  Glu  Leu  Leu  Lys  Lys
               100                     105                     110

Gly  Asn  Ser  Leu  Tyr  Ser  Lys  Val  Ser  Asp  Lys  Val  Phe  Gln  Cys  Leu
               115                     120                     125

Arg  Asp  Thr  Asn  Ser  Arg  Leu  Gly  Leu  Gly  Ser  Glu  Leu  Arg  Glu  Asp
130                      135                     140

Ile  Lys  Glu  Lys  Val  Ile  Asn  Leu  Gly  Val  Tyr  Met  His  Ser  Ser  Gln
145                      150                     155                     160

Trp  Phe  Glu  Pro  Phe  Leu  Phe  Trp  Phe  Thr  Val  Lys  Thr  Glu  Met  Arg
               165                     170                     175

Ser  Val  Ile  Lys  Ser  Gln  Thr  His  Thr  Cys  His  Arg  Arg  Arg  His  Thr
               180                     185                     190

Pro  Val  Phe  Phe  Thr  Gly  Ser  Ser  Val  Glu  Leu  Leu  Ile  Ser  Arg  Asp
               195                     200                     205

Leu  Val  Ala  Ile  Ile  Ser  Lys  Glu  Ser  Gln  His  Val  Tyr  Tyr  Leu  Thr
          210                     215                     220

Phe  Glu  Leu  Val  Leu  Met  Tyr  Cys  Asp  Val  Ile  Glu  Gly  Arg  Leu  Met
225                      230                     235                     240

Thr  Glu  Thr  Ala  Met  Thr  Ile  Asp  Ala  Arg  Tyr  Thr  Glu  Leu  Leu  Gly
               245                     250                     255

Arg  Val  Arg  Tyr  Met  Trp  Lys  Leu  Ile  Asp  Gly  Phe  Phe  Pro  Ala  Leu
               260                     265                     270

Gly  Asn  Pro  Thr  Tyr  Gln  Ile  Val  Ala  Met  Leu  Glu  Pro  Leu  Ser  Leu
```

-continued

|     | 275 |     |     |     |     | 280 |     |     |     |     | 285 |     |     |     |
|-----|-----|-----|-----|-----|-----|-----|-----|-----|-----|-----|-----|-----|-----|-----|
| Ala | Tyr 290 | Leu | Gln | Leu | Arg | Asp 295 | Ile | Thr | Val | Glu | Leu 300 | Arg | Gly | Ala | Phe |
| Leu 305 | Asn | His | Cys | Phe | Thr 310 | Glu | Ile | His | Asp | Val 315 | Leu | Asp | Gln | Asn | Gly 320 |
| Phe | Ser | Asp | Glu | Gly 325 | Thr | Tyr | His | Glu | Leu 330 | Ile | Glu | Ala | Leu | Asp 335 | Tyr |
| Ile | Phe | Ile | Thr 340 | Asp | Asp | Ile | His | Leu 345 | Thr | Gly | Glu | Ile | Phe 350 | Ser | Phe |
| Phe | Arg | Ser 355 | Phe | Gly | His | Pro | Arg 360 | Leu | Glu | Ala | Val | Thr 365 | Ala | Ala | Glu |
| Asn | Val 370 | Arg | Lys | Tyr | Met | Asn 375 | Gln | Pro | Lys | Val | Ile 380 | Val | Tyr | Glu | Thr |
| Leu 385 | Met | Lys | Gly | His | Ala 390 | Ile | Phe | Cys | Gly | Ile 395 | Ile | Ile | Asn | Gly | Tyr 400 |
| Arg | Asp | Arg | His | Gly 405 | Gly | Ser | Trp | Pro | Pro 410 | Leu | Thr | Leu | Pro | Leu 415 | His |
| Ala | Ala | Asp | Thr 420 | Ile | Arg | Asn | Ala | Gln 425 | Ala | Ser | Gly | Glu | Gly 430 | Leu | Thr |
| His | Glu | Gln | Cys 435 | Val | Asp | Asn | Trp | Lys 440 | Ser | Phe | Ala | Gly | Val 445 | Lys | Phe |
| Gly | Cys 450 | Phe | Met | Pro | Leu | Ser 455 | Leu | Asp | Ser | Asp | Leu 460 | Thr | Met | Tyr | Leu |
| Lys 465 | Asp | Lys | Ala | Leu | Ala 470 | Ala | Leu | Gln | Arg | Glu 475 | Trp | Asp | Ser | Val | Tyr 480 |
| Pro | Lys | Glu | Phe | Leu 485 | Arg | Tyr | Asp | Pro | Pro 490 | Lys | Gly | Thr | Gly | Ser 495 | Arg |
| Arg | Leu | Val | Asp 500 | Val | Phe | Leu | Asn | Asp 505 | Ser | Ser | Phe | Asp | Pro 510 | Tyr | Asp |
| Val | Ile | Met | Tyr 515 | Val | Val | Ser | Gly | Ala 520 | Tyr | Leu | His | Asp | Pro 525 | Glu | Phe |
| Asn | Leu 530 | Ser | Tyr | Ser | Leu | Lys 535 | Glu | Lys | Glu | Ile | Lys 540 | Glu | Thr | Gly | Arg |
| Leu 545 | Phe | Ala | Lys | Met | Thr 550 | Tyr | Lys | Met | Arg | Ala 555 | Cys | Gln | Val | Ile | Ala 560 |
| Glu | Asn | Leu | Ile | Ser 565 | Asn | Gly | Ile | Gly | Lys 570 | Tyr | Phe | Lys | Asp | Asn 575 | Gly |
| Met | Ala | Lys | Asp 580 | Glu | His | Asp | Leu | Thr 585 | Lys | Ala | Leu | His | Thr 590 | Leu | Ala |
| Val | Ser | Gly 595 | Val | Pro | Lys | Asp | Leu 600 | Lys | Glu | Ser | His | Arg 605 | Gly | Gly | Pro |
| Val | Leu | Lys 610 | Thr | Tyr | Ser | Arg | Ser 615 | Pro | Val | His | Thr 620 | Ser | Thr | Arg | Asn |
| Val 625 | Arg | Ala | Ala | Lys | Gly 630 | Phe | Ile | Gly | Phe | Pro 635 | Gln | Val | Ile | Arg | Gln 640 |
| Asp | Gln | Asp | Thr | Asp 645 | His | Pro | Glu | Asn | Met 650 | Glu | Ala | Tyr | Glu | Thr 655 | Val |
| Ser | Ala | Phe | Ile 660 | Thr | Thr | Asp | Leu | Lys 665 | Lys | Tyr | Cys | Leu | Asn 670 | Trp | Arg |
| Tyr | Glu | Thr 675 | Ile | Ser | Leu | Phe | Ala 680 | Gln | Arg | Leu | Asn | Glu 685 | Ile | Tyr | Gly |
| Leu | Pro | Ser 690 | Phe | Phe | Gln | Trp | Leu 695 | His | Lys | Arg | Leu | Glu 700 | Thr | Ser | Val |

-continued

| | | | | | | | | | | | | | | |
|---|---|---|---|---|---|---|---|---|---|---|---|---|---|---|
| Leu | Tyr | Val | Ser | Asp | Pro | His | Cys | Pro | Pro | Asp | Leu | Asp | Ala | His | Ile |
| 705 | | | | 710 | | | | | 715 | | | | | 720 |
| Pro | Leu | Tyr | Lys | Val | Pro | Asn | Asp | Gln | Ile | Phe | Ile | Lys | Tyr | Pro | Met |
| | | | | 725 | | | | 730 | | | | | 735 | |
| Gly | Gly | Ile | Glu | Gly | Tyr | Cys | Gln | Lys | Leu | Trp | Thr | Ile | Ser | Thr | Ile |
| | | | 740 | | | | | 745 | | | | | 750 | | |
| Pro | Tyr | Leu | Tyr | Leu | Ala | Ala | Tyr | Glu | Ser | Gly | Val | Arg | Ile | Ala | Ser |
| | | 755 | | | | | 760 | | | | | 765 | | | |
| Leu | Val | Gln | Gly | Asp | Asn | Gln | Thr | Ile | Ala | Val | Thr | Lys | Arg | Val | Pro |
| | 770 | | | | | 775 | | | | | 780 | | | | |
| Ser | Thr | Trp | Pro | Tyr | Asn | Leu | Lys | Lys | Arg | Glu | Ala | Ala | Arg | Val | Thr |
| 785 | | | | | 790 | | | | 795 | | | | | | 800 |
| Arg | Asp | Tyr | Phe | Val | Ile | Leu | Arg | Gln | Arg | Leu | His | Asp | Ile | Gly | His |
| | | | | 805 | | | | | 810 | | | | | 815 | |
| His | Leu | Lys | Ala | Asn | Glu | Thr | Ile | Val | Ser | Ser | His | Phe | Phe | Val | Tyr |
| | | | 820 | | | | | 825 | | | | | 830 | | |
| Ser | Lys | Gly | Ile | Tyr | Tyr | Asp | Gly | Leu | Leu | Val | Ser | Gln | Ser | Leu | Lys |
| | | 835 | | | | | 840 | | | | | 845 | | | |
| Ser | Ile | Ala | Arg | Cys | Val | Phe | Trp | Ser | Glu | Thr | Ile | Val | Asp | Glu | Thr |
| | 850 | | | | | 855 | | | | | 860 | | | | |
| Arg | Ala | Ala | Cys | Ser | Asn | Ile | Ala | Thr | Thr | Met | Ala | Lys | Ser | Ile | Glu |
| 865 | | | | | 870 | | | | | 875 | | | | | 880 |
| Arg | Gly | Tyr | Asp | Arg | Tyr | Leu | Ala | Tyr | Ser | Leu | Asn | Val | Leu | Lys | Val |
| | | | | 885 | | | | | 890 | | | | | 895 | |
| Ile | Gln | Gln | Ile | Leu | Ile | Ser | Leu | Gly | Phe | Thr | Ile | Asn | Ser | Thr | Met |
| | | | 900 | | | | | 905 | | | | | 910 | | |
| Thr | Arg | Asp | Val | Val | Ile | Pro | Leu | Leu | Thr | Asn | Asn | Asp | Leu | Leu | Ile |
| | | 915 | | | | | 920 | | | | | 925 | | | |
| Arg | Met | Ala | Leu | Leu | Pro | Ala | Pro | Ile | Gly | Gly | Met | Asn | Tyr | Leu | Asn |
| | 930 | | | | | 935 | | | | | 940 | | | | |
| Met | Ser | Arg | Leu | Phe | Val | Arg | Asn | Ile | Gly | Asp | Pro | Val | Thr | Ser | Ser |
| 945 | | | | | 950 | | | | | 955 | | | | | 960 |
| Ile | Ala | Asp | Leu | Lys | Arg | Met | Ile | Leu | Ala | Ser | Leu | Met | Pro | Glu | Glu |
| | | | | 965 | | | | | 970 | | | | | 975 | |
| Thr | Leu | His | Gln | Val | Met | Thr | Gln | Gln | Pro | Gly | Asp | Ser | Ser | Phe | Leu |
| | | | 980 | | | | | 985 | | | | | 990 | | |
| Asp | Trp | Ala | Ser | Asp | Pro | Tyr | Ser | Ala | Asn | Leu | Val | Cys | Val | Gln | Ser |
| | | | 995 | | | | | 1000 | | | | | 1005 | | |
| Ile | Thr | Arg | Leu | Leu | Lys | Asn | Ile | Thr | Ala | Arg | Phe | Val | Leu | Ile | His |
| | | 1010 | | | | | 1015 | | | | | 1020 | | | |
| Ser | Pro | Asn | Pro | Met | Leu | Lys | Gly | Leu | Phe | His | Asp | Asp | Ser | Lys | Glu |
| 1025 | | | | 1030 | | | | | 1035 | | | | | | 1040 |
| Glu | Asp | Glu | Gly | Leu | Ala | Ala | Phe | Leu | Met | Asp | Arg | His | Ile | Ile | Val |
| | | | | 1045 | | | | | 1050 | | | | | 1055 | |
| Pro | Arg | Ala | Ala | His | Glu | Ile | Leu | Asp | His | Ser | Val | Thr | Gly | Ala | Arg |
| | | | | 1060 | | | | | 1065 | | | | | 1070 | |
| Glu | Ser | Ile | Ala | Gly | Met | Leu | Asp | Thr | Thr | Lys | Gly | Leu | Ile | Arg | Ala |
| | | | 1075 | | | | | 1080 | | | | | 1085 | | |
| Ser | Met | Arg | Lys | Gly | Gly | Leu | Thr | Ser | Arg | Val | Ile | Thr | Arg | Leu | Ser |
| | | 1090 | | | | | 1095 | | | | | 1100 | | | |
| Asn | Tyr | Asp | Tyr | Glu | Gln | Phe | Arg | Ala | Gly | Met | Val | Leu | Leu | Thr | Gly |
| 1105 | | | | | 1110 | | | | | 1115 | | | | | 1120 |
| Arg | Lys | Arg | Asn | Val | Leu | Ile | Asp | Lys | Glu | Ser | Cys | Ser | Val | Gln | Leu |
| | | | | 1125 | | | | | 1130 | | | | | 1135 | |

```
Ala Arg Ala Leu Arg Ser His Met Trp Ala Arg Leu Ala Arg Gly Arg
             1140                1145                1150

Pro Ile Tyr Gly Leu Glu Val Pro Asp Val Leu Glu Ser Met Arg Gly
             1155                1160                1165

His Leu Ile Arg Arg His Glu Thr Cys Val Ile Cys Glu Cys Gly Ser
             1170                1175                1180

Val Asn Tyr Gly Trp Phe Phe Val Pro Ser Gly Cys Gln Leu Asp Asp
1185             1190                1195                     1200

Ile Asp Lys Glu Thr Ser Ser Leu Arg Val Pro Tyr Ile Gly Ser Thr
             1205                1210                1215

Thr Asp Glu Arg Thr Asp Met Lys Leu Ala Phe Val Arg Ala Pro Ser
             1220                1225                1230

Arg Ser Leu Arg Ser Ala Val Arg Ile Ala Thr Val Tyr Ser Trp Ala
             1235                1240                1245

Tyr Gly Asp Asp Asp Ser Ser Trp Asn Glu Ala Trp Leu Leu Ala Arg
             1250                1255                1260

Gln Arg Ala Asn Val Ser Leu Glu Glu Leu Arg Val Ile Thr Pro Ile
1265             1270                1275                     1280

Ser Thr Ser Thr Asn Leu Ala His Arg Leu Arg Asp Arg Ser Thr Gln
             1285                1290                1295

Val Lys Tyr Ser Gly Thr Ser Leu Val Arg Val Ala Arg Tyr Thr Thr
             1300                1305                1310

Ile Ser Asn Asp Asn Leu Ser Phe Val Ile Ser Asp Lys Lys Val Asp
             1315                1320                1325

Thr Asn Phe Ile Tyr Gln Gln Gly Met Leu Leu Gly Leu Gly Val Leu
             1330                1335                1340

Glu Thr Leu Phe Arg Leu Glu Lys Asp Thr Gly Ser Ser Asn Thr Val
1345             1350                1355                     1360

Leu His Leu His Val Glu Thr Asp Cys Cys Val Ile Pro Met Ile Asp
             1365                1370                1375

His Pro Arg Ile Pro Ser Ser Arg Lys Leu Glu Leu Arg Ala Glu Leu
             1380                1385                1390

Cys Thr Asn Pro Leu Ile Tyr Asp Asn Ala Pro Leu Ile Asp Arg Asp
             1395                1400                1405

Thr Thr Arg Leu Tyr Thr Gln Ser His Arg Arg His Leu Val Glu Phe
             1410                1415                1420

Val Thr Trp Ser Thr Pro Gln Leu Tyr His Ile Leu Ala Lys Ser Thr
1425             1430                1435                     1440

Ala Leu Ser Met Ile Asp Leu Val Thr Lys Phe Glu Lys Asp His Met
             1445                1450                1455

Asn Glu Ile Ser Ala Leu Ile Gly Asp Asp Asp Ile Asn Ser Phe Ile
             1460                1465                1470

Thr Glu Phe Leu Val Ile Glu Pro Arg Leu Phe Thr Ile Tyr Leu Gly
             1475                1480                1485

Gln Cys Ala Ala Ile Asn Trp Ala Phe Asp Val His Tyr His Arg Pro
             1490                1495                1500

Ser Gly Lys Tyr Gln Met Gly Glu Leu Leu Ser Ser Phe Leu Ser Arg
1505             1510                1515                     1520

Met Ser Lys Gly Val Phe Lys Val Leu Val Asn Ala Leu Ser His Pro
             1525                1530                1535

Lys Ile Tyr Lys Lys Phe Trp His Cys Gly Ile Ile Glu Pro Ile His
             1540                1545                1550

Gly Pro Ser Leu Asp Ala Gln Asn Leu His Thr Thr Val Cys Asn Met
```

```
                    1555                  1560                  1565
Val  Tyr  Thr  Cys  Tyr  Met  Thr  Tyr  Leu  Asp  Leu  Leu  Leu  Asn  Glu  Glu
               1570                  1575                  1580
Leu  Glu  Glu  Phe  Thr  Phe  Leu  Leu  Cys  Glu  Ser  Asp  Glu  Asp  Val  Val
1585                  1590                  1595                  1600
Pro  Asp  Arg  Phe  Asp  Asn  Ile  Gln  Ala  Lys  His  Leu  Cys  Val  Leu  Ala
                    1605                  1610                  1615
Asp  Leu  Tyr  Cys  Gln  Pro  Gly  Ala  Cys  Pro  Pro  Ile  Arg  Gly  Leu  Arg
               1620                  1625                  1630
Pro  Val  Glu  Lys  Cys  Ala  Val  Leu  Thr  Asp  His  Ile  Lys  Ala  Glu  Ala
          1635                  1640                  1645
Arg  Leu  Ser  Pro  Ala  Gly  Ser  Ser  Trp  Asn  Ile  Asn  Pro  Ile  Ile  Val
          1650                  1655                  1660
Asp  His  Tyr  Ser  Cys  Ser  Leu  Thr  Tyr  Leu  Arg  Arg  Gly  Ser  Ile  Lys
1665                  1670                  1675                  1680
Gln  Ile  Arg  Leu  Arg  Val  Asp  Pro  Gly  Phe  Ile  Phe  Asp  Ala  Leu  Ala
                    1685                  1690                  1695
Glu  Val  Asn  Val  Ser  Gln  Pro  Lys  Ile  Gly  Ser  Asn  Asn  Ile  Ser  Asn
               1700                  1705                  1710
Met  Ser  Ile  Lys  Ala  Phe  Arg  Pro  Pro  His  Asp  Asp  Val  Ala  Lys  Leu
               1715                  1720                  1725
Leu  Lys  Asp  Ile  Asn  Thr  Ser  Lys  His  Asn  Leu  Pro  Ile  Ser  Gly  Gly
          1730                  1735                  1740
Asn  Leu  Ala  Asn  Tyr  Glu  Ile  His  Ala  Phe  Arg  Arg  Ile  Gly  Leu  Asn
1745                  1750                  1755                  1760
Ser  Ser  Ala  Cys  Tyr  Lys  Ala  Val  Glu  Ile  Ser  Thr  Leu  Ile  Arg  Arg
               1765                  1770                  1775
Cys  Leu  Glu  Pro  Gly  Glu  Asp  Gly  Leu  Phe  Leu  Gly  Glu  Gly  Ser  Gly
          1780                  1785                  1790
Ser  Met  Leu  Ile  Thr  Tyr  Lys  Glu  Ile  Leu  Lys  Leu  Asn  Lys  Cys  Phe
               1795                  1800                  1805
Tyr  Asn  Ser  Gly  Val  Ser  Ala  Asn  Ser  Arg  Ser  Gly  Gln  Arg  Glu  Leu
          1810                  1815                  1820
Ala  Pro  Tyr  Pro  Ser  Glu  Val  Gly  Leu  Val  Glu  His  Arg  Met  Gly  Val
1825                  1830                  1835                  1840
Gly  Asn  Ile  Val  Lys  Val  Leu  Phe  Asn  Gly  Arg  Pro  Glu  Val  Thr  Trp
               1845                  1850                  1855
Val  Gly  Ser  Val  Asp  Cys  Phe  Asn  Phe  Ile  Val  Ser  Asn  Ile  Pro  Thr
               1860                  1865                  1870
Ser  Ser  Val  Gly  Phe  Ile  His  Ser  Asp  Ile  Glu  Thr  Leu  Pro  Asn  Lys
          1875                  1880                  1885
Asp  Thr  Ile  Glu  Lys  Leu  Glu  Glu  Leu  Ala  Ala  Ile  Leu  Ser  Met  Ala
          1890                  1895                  1900
Leu  Leu  Leu  Gly  Lys  Ile  Gly  Ser  Ile  Leu  Val  Ile  Lys  Leu  Met  Pro
1905                  1910                  1915                  1920
Phe  Ser  Gly  Asp  Phe  Val  Gln  Gly  Phe  Ile  Ser  Tyr  Val  Gly  Ser  Tyr
               1925                  1930                  1935
Tyr  Arg  Glu  Val  Asn  Leu  Val  Tyr  Pro  Arg  Tyr  Ser  Asn  Phe  Ile  Ser
               1940                  1945                  1950
Thr  Glu  Ser  Tyr  Leu  Val  Met  Thr  Asp  Leu  Lys  Ala  Asn  Arg  Leu  Met
          1955                  1960                  1965
Asn  Pro  Glu  Lys  Ile  Lys  Gln  Gln  Ile  Ile  Glu  Ser  Ser  Val  Arg  Thr
          1970                  1975                  1980
```

Ser Pro Gly Leu Ile Gly His Ile Leu Ser Ile Lys Gln Leu Ser Cys
1985                    1990                1995                    2000

Ile Gln Ala Ile Val Gly Asp Val Val Ser Arg Gly Asp Ile Asn Pro
            2005                2010                2015

Thr Leu Lys Lys Leu Thr Pro Ile Glu Gln Val Leu Ile Asn Cys Gly
            2020                2025                2030

Leu Ala Ile Asn Gly Pro Lys Leu Cys Lys Glu Leu Ile His His Asp
            2035            2040                2045

Val Ala Ser Gly Gln Asp Gly Leu Leu Asn Ser Ile Leu Ile Leu Tyr
    2050                2055                2060

Arg Glu Leu Ala Arg Phe Lys Asp Asn Arg Arg Ser Gln Gln Gly Met
2065                2070                2075                2080

Phe His Ala Tyr Pro Val Leu Val Ser Ser Arg Gln Arg Glu Leu Ile
                2085                2090                2095

Ser Arg Ile Thr Arg Lys Phe Trp Gly His Ile Leu Leu Tyr Ser Gly
            2100                2105                2110

Asn Arg Lys Leu Ile Asn Lys Phe Ile Gln Asn Leu Lys Ser Gly Tyr
        2115                2120                2125

Leu Ile Leu Asp Leu His Gln Asn Ile Phe Val Lys Asn Leu Ser Lys
    2130                2135                2140

Ser Glu Lys Gln Ile Ile Met Thr Gly Gly Leu Lys Arg Glu Trp Val
2145                2150                2155                2160

Phe Lys Val Thr Val Lys Glu Thr Lys Glu Trp Tyr Lys Leu Val Gly
                2165                2170                2175

Tyr Ser Ala Leu Ile Lys Asp
                2180

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TTAGGGATAT CCGAGATGGC CACAC        25

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CTCGGAAGAA CAAGGCTCAG ACAC        24

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GGAAGGACAC CTCTCAAGCA TCATG  25

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCAGCCATCA GTTCCTCAAG  20

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GTCTACATCC TGATTGCAGT G  21

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GTCAACGAGG AAGATCCGTG AACTCCTCA  29

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GCACGATTTG ACTAAGGCAC TCCA  24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TGTCCTCATT GACAAAGAGT CATG  24

( 2 ) INFORMATION FOR SEQ ID NO:16:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

AGGTGCTTGT CAATGCTCTA AGCCA     25

( 2 ) INFORMATION FOR SEQ ID NO:17:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

CTTATCGATG GCTCTGCTCC TGGGC     25

( 2 ) INFORMATION FOR SEQ ID NO:18:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

TGGAAGCTTA TCCAGAATCT CAAGTCCGGC T     31

( 2 ) INFORMATION FOR SEQ ID NO:19:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:19:

CTGTGAATTC TGCAGGATCC TTTTTT     27

ATTENUATED MEASLES VIRUS VACCINE, CONTAINING SPECIFIC NUCLEOTIDE SEQUENCE AND A METHOD FOR ITS ABSOLUTE IDENTIFICATION

This application is a continuation of application Ser No. 07/848,400, filed Mar. 10, 1992, now abandoned.

BACKGROUND OF THE INVENTION

1. Field of the Invention

The present invention relates to a strain of measles virus vaccine comprising a specific nucleotide sequence, and a method for its absolute identification.

2. Description of the Prior Art

Measles virus is the causative virus of measles, and belongs to the Paramyxoviridae family of RNA virus.

The first isolation of measles virus from patients using a primary culture of human kidney cells was made by J. F. Enders et al. in 1954 (Enders, J. F. et al., Proc. Soc. Exp. Biol. Med., Vol. 86, pp. 227–286, 1954). Attenuated measles virus vaccine was developed using the isolated Edmonston strain by Enders et al. (Enders, J. F. et al., New England J. Med., Vol. 263, pp. 153–259, 1960). However, the vaccine developed by Enders et al. frequently induced adverse effects including pyrogenicity and exanthema.

Many strains of attenuated measles virus having been established by further attenuation of the Edmonston strain. Among these strains the Schwarz strain established by A. J. F. Schwarz has been commonly used for live measles vaccines.

The present inventors have isolated four strains of a cold variant derived from attenuated measles virus of the Edmonston strain, supplied by Dr. Enders (Makino, S. et al., Jap. J. Microbiol., Vol 14, pp. 501–504, 1970).

Reduction of immunogenicity, i.e. effectiveness, according to a development of attenuation of measles virus has generally been known. Among the strains of the isolated cold variant, a viral strain which grows adaptively at 33° C. was found to be a further attenuated measles virus with high immunogenicity having properties different from those generally observed in the conventional measles virus (Makino, S. et al., Jap. J. Microbiol., Vol. 17, pp. 75–79, 1973).

In order to develop the seeds for live measles vaccines from the cold variant, one of the present inventors has isolated clone virus which is a strain adapted with chick embryo cells obtained from specific pathogen-free eggs, having the same temperature marker, and designated as the AIK-C strain (Sasaki K., Kitasato Arch. Exp. Med., Vol. 47, pp. 1–12, 1974).

The pyrogenicity ratio (≦37.5° C.) of an AIK-C strain live vaccine produced from the seeds of AIK-C strain in measles-sensitive infants approximately ⅓–¼ as compared with that of Schwarz strain vaccine. The AIK-C strain has been found to be a further attenuated measles virus than the Schwarz strain, with the unique characteristic of having a high immunogenicity response without lowering immunogenicity (Makino, S. et al., Kitasato Arch. Exp. Med., Vol. 47, pp. 13–21, 1974).

Encephalitis that seems to be caused by administered live measles vaccine has been observed in 1–3 persons per million treated infants. However, this neurological complication has never been reported in the case of the AIK-C strain in spite of the administration of AIK-C strain live measles vaccine to ten million people in Japan (Hirayama, M. et al., Inf. Dis., Vol. 5, pp. 495–503, 1983; Makino, S., Vol. 5, pp. 504–505, 1983).

SUMMARY AND OBJECTS OF THE INVENTION

The biological properties of the AIK-C strain are unique, and differ markedly from those of the other strains of measles virus. However, the virus is easily mutated and even in an attenuated measles virus strain such as the AIK-C strain, a small degree of formation of variant strains can be observed during the growth phase. Accordingly, during the production of live measles vaccine, the quality control for comparing the respective identities of the seed virus and the vaccine virus produced therefrom is the most important procedure.

As noted above, a temperature marker test for the AIK-C strain has been applied as a quality control test (Sasaki, K., Kitasato Arch. Exp. Med., Vol. 47, pp. 1–12, 1974). However that biological assay method does not always provide absolute identification of the AIK-C strain.

The fundamental biological properties of the virus depend on its genome, which consist of nucleic acid of viral particles. The nucleic acid of measles virus consists of single strain (−)RNA, and each viral strain has its own nucleic acid made up of a specific nucleotide sequence.

Complete differential identification between viral trains is, therefore, necessary to determine the nucleotide sequence of viral nucleic acid in the strain. The present inventors have focused on this point, and have analyzed the nucleotide sequence of nucleic acid relating to measles virus infection. In the course of that analysis, the inventors have provided an administrative control method for producing a stable AIK-C strain of measles virus without variants or mutation.

The known identification methods for various measles strain apply a specific biological response test for the virus strain in question; however, these are not methods capable of absolute identification. For quality control during production of the AIK-C strain vaccine, the aforementioned temperature marker test has been applied. The present inventors, on the other hand, have determined the entire nucleotide sequence of the AIK-C strain virus genome, thereby to establish an absolute identification method for the said identification test. Since the entire specific nucleotide sequence, consisting of 15,894 bases in AIK-C strain, has been clearly determined, the virus can be identified at the genetic level, and the identification technique can therefore provide an absolute determination, so that quality control on a stable AIK-C strain vaccine can easily and exactly be performed.

Therefore an object of the present invention is to provide an attenuated live measles vaccine comprising a specific nucleotide sequence.

Another object of the present invention is to provide an absolute identification method for a measles virus strain.

A further object according to the present invention is to provide a measles vaccine virus genomic DNA consisting of the nucleotide sequence described below, with partial insertion mutational sequence or defective sequence.

A still further object of the invention is to provide an absolute identification method for a measles vaccine virus strain, which comprises detecting a specific nucleotide sequence consisting of the 15,894 nucleotides listed below coded by the genomic RNA of measles vaccine virus strain.

A yet still further object of the invention is to provide an absolute identification method comprising detecting a part of the nucleotide sequence of viral genomic DNA by the Northern blot technique and polymerase chain reaction method.

BRIEF DESCRIPTION OF THE DRAWINGS

The above and other objects and advantages according to the invention will be more readily apparent from a reading of the following detailed discussion taken with reference to the accompanying drawings, in which:

FIG. 3 is a genomic DNA sequence of the synthetic oligonucleotides (SEQ ID NOS:8–14) as complementary genome DNA.

DETAILED DISCUSSION

The inventors have determined that the complete cDNA sequence coded by the RNA genome of the AIK-C strain is as follows as shown in SEQ ID NO:1. The coding regions of SEQ ID NO:1 encode the amino acid sequences of SEQ ID NOS:2–7

The physical characteristics of the sequence are:
Sequence type: nucleic acid
Strandedness: single
Topology: linear
Molecule type: antigenomic DNA
Original source
Organism: attenuated measles vaccine
Strain: AIK-C According to the present invention, a seed virus of the measles virus AIK-C strain is first used. This vaccine virus is propagated in chick embryo cells derived from specific pathogen-free hen's eggs to prepare so-called bulk vaccine, from which a virus suspension can be prepared by conventional purification techniques. The bulk vaccine can be a part of the virus pool prepared for commercial measles AIK-C strain vaccine.

The clarified virus suspension is purified by ultracentrifugation through continuous sucrose gradients. Virus RNA is extracted by the SDS-phenol method. Synthetic primer can be synthesized with approx. 25 mer synthetic primer by the amidide method.

The deoxyoligonucleotide, a synthetic primer, can be synthesized, for example, on a CYCLONE DNA SYNTHESIZER (Biosearch, Inc.)

The AIK-C virus genome RNA is used as a template for the synthesis of cDNA using the above synthetic oligonucleotide primer. The AIK-C virus genome RNA is reversely transcribed by reverse transcriptase to prepare single-strand cDNA, which is thereafter treated by the RNase H method to prepare double-strand cDNA. The double-stranded cDNAs are treated with appropriate restriction enzymes and are inserted into pUC plasmids (pUC 18 or pUC 19).

Figure 1:
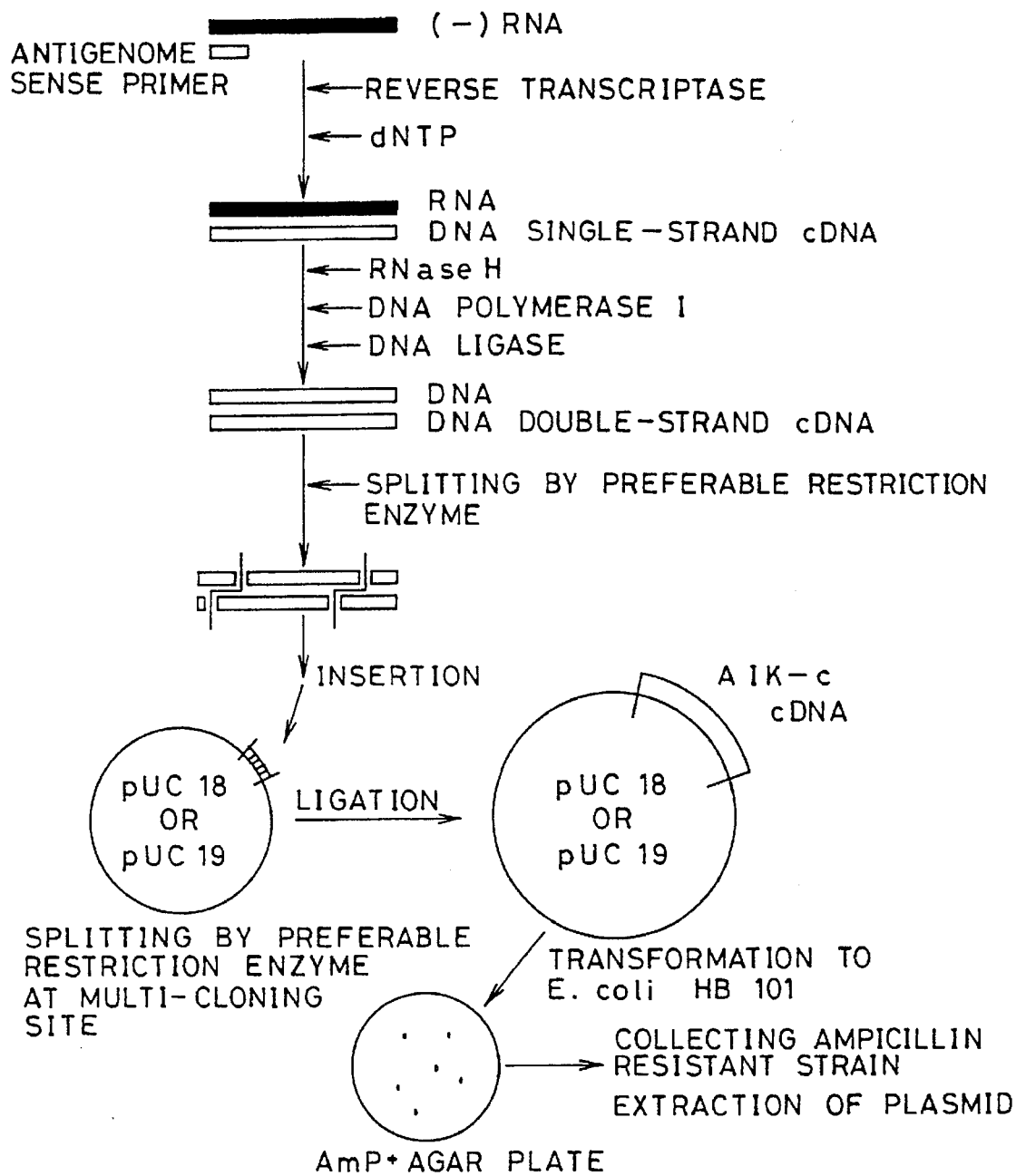
FIG. 1 is an outline of cDNA construction.
Figure 2:
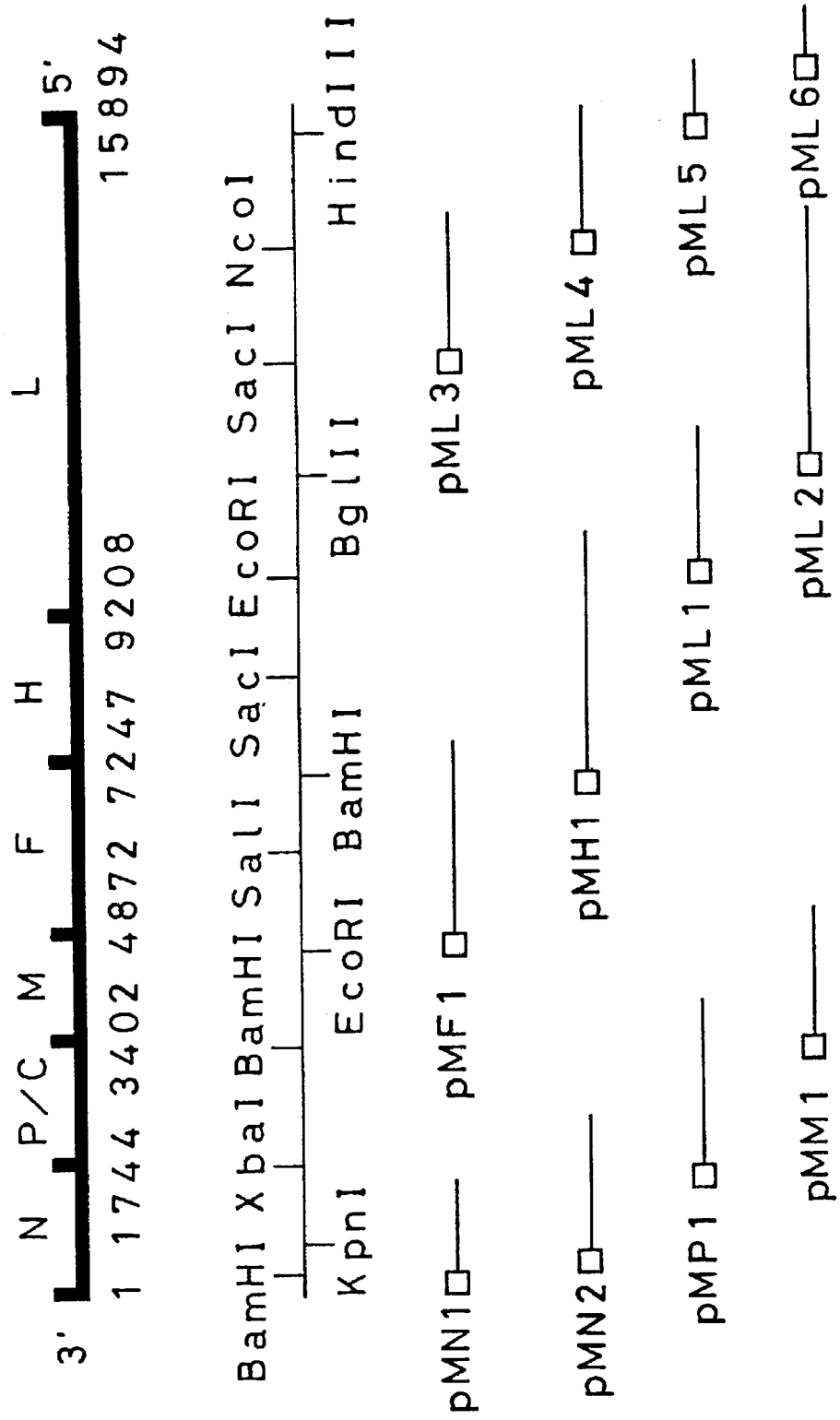
FIG. 2 is a mapping of cDNA clones of the AIK-C.

The above process is illustrated schematically in FIG. 1.

E. coli K 12 strain HB101 is transformed with the resulting recombinant plasmid. The transformants are selected according to their ampicillin resistance. Colonies containing recombinant plasmids are screened by measuring the size of plasmic DNA by agarose gel electrophoresis. To determine the AIK-C genome sequence, the cDNA are subcloned into the bacteriophage M 13 series, and the single-strand M 13 phage DNAs are isolated from candidate subclones.

Determination of the obtained cDNA clone can be made using several restriction enzyme cleavage types. In the cDNA obtained using a synthetic primer such as MP-1, the restriction enzyme sites of BamHI, E coRV and Xbal are located. In the plasmid extracted from an ampicillin resistant strain, in case this type of cDNA is observed, approximately 1504 base fragments are identified by splitting with BamHI and Xbal in an agarose gel electrophoresis. Further treatment of these fragments with EcoRV provides two fragments of 650 and 854 base fragments.

Accordingly, an identification of the obtained cDNA clone is made by cleaving the inserted fragment in the plasmid and determining its size, or by determining the specific restriction site of measles DNA in the fragments.

To determine the base sequence, the cDNA, which are split by restriction enzymes to prepare cohesive ends or blunt ends, is inserted into M 13 phage vectors whose cloning parts are cleaved by the appropriate restriction enzymes. The phage containing the thus-prepared recombinant DNA is infected into E. coli. Single-strand recombinant DNA is extracted from the infected phage plaques, and the nucleotide sequence thereof is determined by the dideoxy chain termination method (dideoxy sequence method).

A primer such as pMN 2, the cDNA obtained from MP-1, is split by BamHI and Xbal, and is cloned with pUC plasmid. After determining the cDNA, the DNA fragment originated from AIK-C strain by splitting with the same restriction enzyme, further the fragment is split using EcoRV to prepare two fragments consisting of 650 bp and 854 bp.

These fragments are ligated into the M 13 replicative form double-strand DNA, which was previously split by BamHI and Xbal transfected into E. coli. After the recombinant phage is selected, the phage is infected in E. coli and allowed to multiply. Single-strand recombinant DNA is extracted from the supernatant phase of the phage solution and the nucleotide sequence thereof is determined by the dideoxy sequence method.

The viral genome of the AIK-C strain has been found to be constructed of 15,894 nucleotides and its entire sequence is shown in the sequence given above. A measles virus containing this RNA genome has the superior properties of AIK-C virus strain. The specific nucleotide sequence of AIK-C virus strain genome is determined by the PCR method and can be compared with the virus strain whether the strain is to be used for AIK-C strain virus vaccine or whether the prepared AIK-C strain virus vaccine is simply the maintaining properties of AIK-C strain. Furthermore, if an infant to whom the measles vaccine has been administered exhibits exanthema and antibodies against measles virus are observed in the lymphocyte of the infant, the causes thereof can be determined by comparing with the nucleotide sequence, as to whether the exanthema is caused by the administered vaccine or not.

The following examples are provided to illustrate the present invention but are not to be construed as limiting.

EXAMPLE 1

Determination of the Nucleotide Sequence of a Virus Obtained from AIK-C Virus Strain Bulk Vaccine Step a:

A seed virus of the AIK-C measles strain (Seed Lot 0–2) was inoculated up to an infectivity titer of 0.05 in chick embryo cells derived from specific pathogen-free hen's eggs cultured in a surface area cell culture (230 cm$^2$) in a large Roux bottle (approx. 1 liter volume). A culture medium (150 ml) of Eagle's minimum essential medium (MEM) containing 1% calf serum was added thereto and the virus was cultured at 33° C.

Step b:

On the third day after inoculation, the cultured medium was removed, and then 150 ml of new medium was added and the cultivation was continued.

Step c:

On the sixth day after inoculation of virus, the culture was removed. The layer of infected chick embryo cells was washed completely three times with 100 ml aliquots of Hank's solution. Cultivation was then continued at 33° C. after adding 200 ml of Eagle's MEM for cell culture, containing 0.1% sodium glutamate.

Step d:

On the tenth day after virus seed inoculation, the specific cytopathogenic effect for measles virus was observed over the entire infected cell layer, and the culture medium was collected to produce the bulk vaccine solution (volume: approx. 200 ml, infectivity titer: $10^{7.2}$ $TCID_{50}$*/ml; *medium tissue culture infective dose).

Step e:

The bulk vaccine solution was centrifuged at 3,000 rpm for 30 mins. and the supernatant solution removed therefrom was further centrifuged at 25,000 rpm for 90 mins. (Beckman. L 8–55 M, rotor: SW 28)

Step f:

After the further supernatant solution was removed, 1 ml of TEN buffer solution (10 mM-Tris HCl, 1 mM-EDTA, 100 mM-NaCl, pH 7.4) was added to the precipitate in each centrifuge tube, and the precipitate was well suspended therein to prepare concentrated virus. Each of the thus-obtained concentrated virus suspensions was adjusted to a final volume of 10 ml by adding TEN buffer solution, to prepare clarified virus suspension.

Step g:

The clarified virus suspension (5 ml) was layered on 30–60% continuous sucrose gradients in two centrifuge tubes (Beckman centrifuge SW 41 rotor), each having 60% (w/v) sucrose solution in TEN buffer solution (6.8 ml) and 30% (w/v) sucrose solution in TEN buffer solution (6.8 ml) per tube, and centrifuged for 90 mins. at 207,000 g and 4° C. The suspension was fractionated and the fractions showing the highest infectivity titer ($10^{8.3}$ $TCID_{50}$/ml) were collected and again centrifuged by the same technique to prepare purified virus particles.

Step h:

The purified virus particles were diluted five-fold with TEN buffer solution, and 200 µl of each was added into a respective 1.5 ml microtesttube, along with 5 µl of 20% SDS, 100 µl phenol and 100 µl chloroform, followed by complete stirring using a vortex mixer. The mixture was further centrifuged at 12,000 rpm for 5 mins. to separate the organic layer and the aqueous layer. The aqueous layer was collected into another 1.5 ml microtesttube and treated twice by phenol extraction (SDS-phenol extraction). The recovered aqueous layer was mixed with 5M-NaCl (1/25 volume), and ethanol (2.5 volume), allowed to stand at −20° C. for 2 hours, then centrifuged at 12,000 rpm for 10 mins. to collect precipitated RNA which was washed with 70% ethanol and dried. The dried material was dissolved in sterilized redistilled water (50 µl) and autoclaved to prepare an RNA suspension.

Step i:

Cyclone DNA synthesizer

Synthetic primer deoxyoligonucleotide, 12 primers comprising approx. 25 mer of MP-1–MP-11 and BEP $(dT)_7$ as shown in FIG. 3 were synthesized using a Cyclone DNA Synthesizer (Biosearch Inc., U.S.A.)

Step j:

10 µl of the RNA suspension obtained in the above Step h (AIK-C virus genome RNA) was used as a template for the synthesis of DNA using 2 µl of the above synthetic oligonucleotide primers, MP-1 or MP-11, and cDNA was prepared by reverse transcriptase treatment. The cDNA was then transferred to double-strand cDNA by using RNase H-DNA polymerase I according to the technique described by Gubler and Hoffman in GENE, Vol. 25, pp. 263–269, (1983).

Step k:

The obtained cDNA was cleaved at each of its restriction enzyme cleavage sites by BamHI-XbaI, XbaI-BamHI, BamHI-EcoRI, EcoRI-BamHI, BamHI-EcoRI, EcoRI, BglII, BglII-SacI and SacI-NcoI-XbaI. Each fragment was inserted into a corresponding cloning site of pUC plasmid (pUC 18 and pUC 19).

Step l:

E. coli HB101 was transformed with the above recombinant plasmid to obtain ampicillin-resistant colonies. A plasmid DNA was extracted from the thus-obtained colonies, and the colonies containing recombinant plasmids were screened by measuring the size length of the plasmid DNA fragments by 0.8% agarose gel electrophoresis.

Step m:

To obtain the 3' terminal clone of the AIK-C genome, poly(A) was tailed at the 3' end of the genomic RNA, an RNA suspension obtained in the above Step h, with poly(A) polymerase and adenosine triphosphate (ATP). The thus-obtained 3'A tailed RNA suspension, i.e. the polyadenylated RNA, was reversely transcribed using $BEP(dT)_7$ primer to prepare cDNA according to the above Step j. The $BEP(dT)_7$ primer has the sequence 5'-CTGTGAATTCTGCAGGATCCTTTTTTT-3' (SEQ/ID NO:19).

Step n:

The 5' terminal clone was synthesized with the primer located close to the 5' terminus. That is, the primer contained complementary DNA in a domain of 15,592–15,615 in the measles virus genome. The synthetic primer has the sequence 5'-TGGAAGCTTATCCAGAATCTCAAGTCCGGCT-3' (SEQ/ID NO:18)

A DNA-RNA hybrid was prepared by using the said synthetic DNA as a primer with reverse transcriptase. After alkaline treatment of the hybrid, poly(dA), i.e. dATP, was tailed to the 3' end of the resulting cDNA with terminal deoxynucleotidyl transferase. It was subsequently converted to the double-stranded cDNA using the $BEP(dT)_7$ primer in the above Step m and the Klenow fragment.

Step o:

The thus-obtained cDNAs were subcloned into the bacteriophage M 13 series vector (mp 18 and mp 19), and the single-strand M 13 phage DNAs were isolated. The nucleotide sequence of those cDNAs was determined with the said single-stranded DNA by means of the dideoxy chain termination method using a 7-DEAZA-dGTP sequencing kit (Takara Shuzo).

Step p:

Computer analysis of the nucleotide and peptide sequence was performed using GENETYX software.

EXAMPLE 2

Determination of the Viral Nucleotide of AIK-C Strain Seed Virus Grown in Vero Cells (African Green Monkey Live Cells Step a:

AIK-C strain seed virus (Seed Lot No. 0–2) was inoculated in Vero cells previously cultured in a large size Roux bottle according to the method described in Example 1, and incubated at 33° C.

Step b:

On the fifth day of incubation, the infected cell layers were washed with Hank's solution, then Eagle's MEM (200 ml) without calf serum was added thereto and the culture was further incubated for two days. The incubated viral culture was collected to obtain a bulk virus suspension (approx. 200 ml, infective titer: $10_{6.5}$ TCID$_{50}$/ml).

Step c:

The bulk vaccine was centrifuged at 3,000 rpm for 30 mins., whereafter the supernatant suspension removed therefrom was centrifuged at 25,000 rpm for 90 mins. (Centrifuge: Beckman L8–55M, rotor: SW 28)

Step d:

After the further supernatant solution was removed, 1 ml of TEN buffer solution (10 mMTris-HCl 1 mM EDTA, 100 mM NaCl, pH 7.4) was added to the precipitate in each centrifuge tube, and the precipitate was suspended completely to prepare concentrated virus material, which was adjusted to a volume of 10 ml by adding TEN buffer solution to prepare the starting material virus suspension.

Step e:

5 ml of the virus suspension starting material was layered on a 30–60% continuous sucrose gradient in each of two tubes consisting of 60% (w/v) sucrose solution (TEN buffer solution) (6.8 ml) and 30% (w/v) sucrose solution (TEN buffer solution) (6.8 ml), then centrifuged at 207,000 g for 90 mins. at 4° C.

The centrifuged suspension in each tube was fractionated by means of a fraction collector and fractions showing high infectivity ($10^{8.3}$ TCID$_{50}$/ml) were collected. The collected fractions were again centrifuged in the same manner to recover purified virus.

Step f:

200 µl of the purified virus, diluted five-fold with TEN buffer solution, was added to each of a series of 1.5 ml microtesttubes. To each tube was then added 5 µl of 20% SDS, 100 µl of phenol and 100 µl chloroform, and the contents of the tubes were completely stirred using a vortex mixer. The organic layer and aqueous layer were separated by centrifuging at 12,000 rpm for 5 mins. The aqueous layer was collected in another 1.5 ml microtesttube, and extracted twice with the same SDS-phenol extractant as above.

The recovered aqueous layer was mixed with 5M NaCl (1/25 volume) and ethanol (2.5 volume), allowed to stand at −20° C. for 2 hours, and centrifuged at 12,000 rpm for 10 mins. to collect precipitated RNA. The precipitated RNA was then washed with 70% ethanol, and dried. An RNA suspension was prepared with sterilization of the dried material and dissolved in redistilled water (50 µl).

Step g:

Cyclone DNA Synthesizer

Synthetic primer deoxyoligonucleotide, 12 primers, comprising approx. 25 mer of MP-1–MP-11 and BEP(dT)$_7$ as shown in FIG. 3 were synthesized using a cyclone DNA synthesizer (Biosearch Inc., U.S.A.)

Step h:

The RNA suspension (10 µl) obtained in the above Example 1 (AIK-C virus genome RNA) was used as a template for the synthesis of cDNA using synthetic oligonucleotide primers (the above synthetic DNA, 2 µl of synthetic primer, MP-1 or MP-11) and cDNA was prepared by reverse transcriptase treatment. The cDNA was then transferred to double-strand cDNA using RNaseH-DNA polymerase I according to the method of Gubler and Hoffman cited above.

Step i:

The obtained cDNA was cleaved at each of its restriction enzyme cleavage sites by BamHI-XbaI, XbaI-BamHI, BamHI-EcoRI, EcoRI-BamHI, BamHI-EcoRI, EcoRI-BglII, BglII-SacI and SacI-NcoI-XbaI. Each fragment was inserted into a corresponding cloning site of pUC plasmid (pUC 18 and pUC 19).

Step j:

*E. coli* HB101 was transformed with the above recombinant plasmid to obtain ampicillin-resistant colonies. A plasmid DNA was extracted from the thus-obtained colonies, and the colonies containing recombinant plasmids were screened by measuring the size length of plasmid DNA fragments by 0.8% agarose gel electrophoresis.

Step k:

To obtain the 3' terminal clone of the AIK-C genome, poly(A) was tailed at the 3' end of the genomic RNA, an RNA suspension obtained in the above Step f, with poly(A) polymerase and adenosine triphosphate (ATP). The thus-obtained 3' tailed RNA suspension, i.e. the polyadenylated RNA, was reversely transcribed using BEP(dT)$_7$ primer to prepare cDNA according to the above Step h. The BEP(dT)$_7$ primer has the sequence 5'-CTGTGAATTCTGCAGGATCCTTTTTTT-3' (SEQ/ID NO:19).

Step l:

The 5' terminal clone was synthesized with the primer located close to the 5' terminals. That is, the primer contained complementary DNA in a domain of 15,592–15,615 in the measles virus genome. The synthetic primer has the sequence 5'-TGGAAGCTTATCCAGAATCTCAAGTCCGGCT-3' (SEQ/ID NO:18).

A DNA-RNA hybrid was prepared by using the said synthetic DNA as a primer with reverse transcriptase. After alkaline treatment of the hybrid, poly(Da), i.e. dATP, was tailed to the 3' end of the resulting cDNA with terminal deoxynucleotidyl transferase. It was subsequently converted to the double-stranded cDNA using the BEP(dT)$_7$ primer in the above Step k and the Klenow fragment.

Step m:

The thus-obtained cDNA were subcloned into the bacteriophage M 13 series vector (mp 18 and mp 19), and the single-stranded M 13 phage DNAs were isolated. The nucleotide sequence of those cDNAs was determined with the said single-stranded DNA by means of the dideoxy chain termination method using a 7-DEAZA-dGTP sequencing kit (Takara Shuzo).

Step n:

Computer analysis of the nucleotide and peptide sequences was performed using GENETYX software.

EXAMPLE 3

Identification by the PCR Method of Measles Virus Obtained from a Patient on the First Day When Measles Symptoms Appeared Step a:

A blood specimen (approx. 5 ml) was collected from a patient on his first day displaying measles exanthema. Lymphocytes were separated using Ficoll (trade name).

Step b:

The lymphocytes were washed twice with PBS. 200 µl of a denaturation solution D (4M guanidium thiocyanate, 25 mM sodium citrate, pH 7.5; 0.5% sarcosine, 0.1M 2-mercapto ethanol) was added thereto. After gentle stirring, 2M sodium acetate (20 µl, pH 4), phenol (200 µl) and chloroform (100 µl), were added in that order.

The mixture was treated with a vortex mixer for 10 sec. and allowed to stand in ice water for 15 mins. Then the mixture was centrifuged at 10,000 g for 20 mins. to recover an aqueous layer. An equal volume of isopropanol was added thereto, and the mixture was allowed to stand at −20° C. for one hour, then centrifuged at 10,000 g for 20 mins. to precipitate RNA. This procedure was performed according to the technique described by Chomoczynski and Sacchi in *Anal. Biochem.*, Vol. 162, pp. 156–159 (1987).

Step c:

The thus-obtained RNA was subjected to a reverse transcriptase reaction and the PCR method.

Step d:

Nucleotide sequencing and identification of the measles virus AIK-C vaccine strain and the naturally-occurring strain performed.

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

---

What is claimed is:

1. A purified and isolated genomic RNA sequence which is the full length complement of the sequence set forth as SEQ ID NO:1.

2. An isolated and purified complementary DNA consisting of the sequence set forth as SEQ ID NO:1.

3. An absolute identification method for a measles vaccine virus strain which comprises isolating the genomic RNA of said measles vaccine virus strain, and comparing the nucleotide sequence of said genomic RNA to the sequence set forth as SEQ ID NO:1 to assess identity therewith.

* * * * *